United States Patent [19]
Haynes

[11] Patent Number: 6,091,000
[45] Date of Patent: Jul. 18, 2000

[54] SCID MOUSE ENGRAFTED WITH HUMAN SYNOVIUM TISSUE

[75] Inventor: Barton F. Haynes, Durham, N.C.

[73] Assignee: Duke University, Durham, N.C.

[21] Appl. No.: 07/933,035

[22] Filed: Aug. 20, 1992

Related U.S. Application Data

[63] Continuation-in-part of application No. 07/669,428, Mar. 15, 1991, abandoned.
[51] Int. Cl.[7] .......................... A01K 67/00; A01K 67/03; A61K 49/00; G01N 33/00
[52] U.S. Cl. .................................... 800/9; 800/3; 424/9.2
[58] Field of Search .................................. 800/2, DIG. 2, 800/3, 8, 9; 424/9, 93 U, 520, 572, 548, 577, 9.2

[56] References Cited

U.S. PATENT DOCUMENTS 5,002,873   3/1991   St. John et al. .

OTHER PUBLICATIONS

Schaible et al (1989) J. Exp. Med. 170, 1427–1432.
Brinckerhoff et al (1981) American J. Pathology 103, 411–419.
Adams et al (1990) Arthritis Rheum. 33 (9 Suppl.), 512.
Haynes et al, "The Role of Leukocyte Adhesion Molecules in Cellular Interactions: Implications for the Pathogenesis of Inflammatory Synovitis", Springer Semin Immunopathol (1989) 11:163–185.
Huet et al, "CD44 Contributes to T Cell Activation[1]", The Journal of Immunology, vol. 143, 798–801, No. 3, Aug. 1, 1989.
Shimizu et al, "Dual Role of the CD44 Molecule in T Cell Adhesion and Activation", The Journal of Immunology, vol. 143, pp. 2457–2463, No. 8, Oct. 15, 1989.
Denning et al, "Antibodies Against the CD44 p80, Lymphocyte Homing Receptor Molecule Augment Human Peripheral Blood T Cell Activiation[1] ", The Journal of Immunology, vol. 144, pp. 7–15, No. 1, Jan. 1, 1990.
Hale et al, "CD44 Antibody Against In(Lu)–Related p80, Lymphocyte–Homing Receptor Molecule Inhibits the Binding of Human Erythrocytes to T Cells[1]", The Journal of Immunology, vol. 143, pp. 3944–3949, No. 12, Dec. 1980.
Kamel–Reid et al, "A Model of Human Acute Lymphoblastic Leukemia in Immune–Deficient SCID Mice", Reports, Science, vol. 246, pp. 1597–1600, Dec. 22, 1989.
Paliard et al, "Evidence for the Effects of a Superantigen in Rheumatoid Arthritis", Reports, Science, vol. 253, pp. 325–329, Jul. 19, 1991.
Choi et al, "Interaction of *Staphylococcus aureus* toxin, "superantigens" with human T cells", Proc. Natl. Acad. Sci. USA, vol. 86, pp. 8941–8945, Nov. 1989.
Wucherpfennig et al, "Shared Human T Cell Receptor $V_\beta$ Usage to Immunodominant Regions of Myelin Basic Protein", Science, vol. 248, pp. 1016–1019, May 25, 1990.

Tighe et al, "Autoantibody production by severe combined immunodeficient mice reconstituted with synovial cells from rheumatoid arthritis patients", Eur. J. Immunol. 1990 20:1843–1848.
McCune et al, "The SCID–hu Mouse: Murine Model for the Analysis of Human Hematolymphoid Differentiation and Function", Science, vol. 241, pp. 1632–1939, Sep. 23, 1988.
Kamel–Reid et al, "Engraftment of Immune–Deficient Mice with Human Hematopoietic Stem Cells", Science, vol. 242, pp. 1706–1709, Dec. 23, 1988.
Abedi et al, "Immunoglobulin production in severe combined immunodeficient (SCID) mice reconstituted with human peripheral blood mononuclear cells", Eur. J. Immunol. 1992, 22:823–828.
Mosier et al, "Transfer of a functional human immune system to mice with severe combined immunodeficiency", Nature, vol. 335, pp. 256–259, Sep. 15, 1988.
Barry et al, "Successful Engraftment of Human Postnatal Thymus in Severe Combined Immune Deficient (SCID) Mice: Differential Engraftment of Thymic Components With Irradiation Versus Anti–asialo GM–1 Immunosuppressive Regimens", J. Exp. Med., vol. 173, pp. 167–180, Jan. 1991.
Krams et al, "Generation of Biliary Lesions After Transfer of Human Lymphocytes Into Severe Combined Immunodeficient (SCID) Mice", J. Exp. Med., vol. 170, pp. 1919–1930, Dec. 1989.
Trentham, David E., "Clues Provided by Animal Models of Arthritis", Pathogenesis of Chronic Inflammatory Arthritis, vo. 14, No. 2, pp. 307–319, Aug. 1987.
Adams et al, "Transplantation of Human Rheumatoid Synovium Into a SCID Mouse as a A Model for Disease Activity", Arthritis Rheum 33(9 Suppl.):5120 (1990).
Denning et al, "Antibodies Against CD44 p80, Lymphocyte Homing Receptor Augment T Cell Activation Via The CD2 Pathway", FASEB J. vol. 3, pA785, 1989 published Feb. 9, 1989.
Hale et al, CD44 Antibody Against In(Lu)–Related p80, Lymphocyte Homing Receptor Molecule Inhibits the Binding of Human Erythrocytes to T Cells, FASEB J. vol. 3, pA482, published Feb. 9, 1989.
Brinckerhoff et al, "Survival of Rheumatoid Synovium Implanted Into Nude Mice", AJP, vol. 103, No. 3, pp. 411–418, Jun. 1981.
Haggi et al, "Restricted heterogeneity in T–cell antigen receptor $V_\beta$ gene usage in the lymph nodes and arthritic joints of mice", Proc. Natl. Acad. Sci USA, vol. 89, pp. 1253–1255, Feb. 1992.

*Primary Examiner*—Deborah Crouch
*Attorney, Agent, or Firm*—Nixon & Vanderhye P.C.

[57] ABSTRACT

The present invention relates, in general, to severe combined immunodeficiency disease (SCID) mice yand, in particular, to SCID mice engrafted with synovium and the methods of using same.

4 Claims, 13 Drawing Sheets

Summary of TCR Vβ Types Found In Normal And B27 Spondyloarthropathy PB T Cells That Had Migrated To Various Types Of Human Synovial Tissue Engrafted Into SCID Mice

| Graft No. | Vβ1 | Vβ2 | Vβ3 | Vβ4 | Vβ5.14 | Vβ5.23 | Vβ6 | Vβ7 | Vβ8 | Vβ9 | Vβ10 | Vβ11 | Vβ12 | Vβ13.1 | Vβ13.2 | Vβ14 | Vβ15 | Vβ16 | Vβ17 | Vβ18 | Vβ19 | Vβ20 | PB T Cell Source | Engrafted Synovium Source |
|---|---|---|---|---|---|---|---|---|---|---|---|---|---|---|---|---|---|---|---|---|---|---|---|---|
| 29-9 | □ | □ | □ | □ | □ | □ | ■ | ■ | ■ | ■ | □ | □ | □ | □ | □ | □ | □ | □ | □ | □ | □ | □ | NI B27 No. 10 | RA No. 29 |
| 29-11 | ■ | □ | □ | ■ | □ | □ | ■ | □ | ■ | □ | □ | □ | □ | □ | □ | ■ | □ | □ | □ | □ | □ | □ | NI B27 No. 10 | RA No. 29 |
| 30-11 | ■ | □ | ■ | ■ | □ | □ | ■ | ■ | ■ | □ | □ | □ | ■ | ■ | □ | □ | □ | □ | ■ | □ | □ | □ | NI B27 No. 10 | RA No. 30 |
| 42-2 | ■ | ■ | ■ | ■ | □ | □ | ■ | ■ | ■ | ■ | □ | ■ | ■ | ■ | ■ | ■ | ■ | □ | ■ | ■ | □ | □ | NI B27 No. 10 | B27 Spondyloarthropathy No. 42 |
| 42-3 | ■ | ■ | ■ | ■ | □ | ■ | ■ | ■ | ■ | □ | ■ | □ | □ | □ | ■ | ■ | ■ | ■ | ■ | ■ | □ | ■ | NI B27 No. 10 | B27 Spondyloarthropathy No. 42 |
| 42-4 | ■ | ■ | ■ | ■ | □ | □ | ■ | ■ | ■ | ■ | ■ | ■ | ■ | ■ | ■ | ■ | □ | ■ | ■ | ■ | ■ | ■ | NI B27 No. 10 | B27 Spondyloarthropathy No. 42 |
| 42-5 | ■ | □ | □ | ■ | □ | □ | □ | □ | □ | ■ | □ | ■ | □ | ■ | ■ | □ | □ | □ | □ | □ | □ | ■ | B27 Spondyloarthropathy No. 42 | B27 Spondyloarthropathy No. 42 |
| Control In Vitro Cultured Cells | | | | | | | | | | | | | | | | | | | | | | | | |
|  | ■ | ■ | ■ | ■ | ■ | ■ | ■ | ■ | ■ | ■ | ■ | ■ | ■ | ■ | ■ | ■ | ■ | ■ | ■ | ■ | ■ | ■ | NI B27 No. 10 After 2 Weeks of In Vitro Culture | |
|  | ■ | ■ | ■ | ■ | ■ | ■ | ■ | ■ | ■ | ■ | ■ | ■ | ■ | ■ | ■ | ■ | ■ | ■ | ■ | ■ | ■ | ■ | B27 Spondyloarthropathy No. 42 After 2 Weeks of In Vitro Culture | |

*Fig. 12D*

SCID MOUSE ENGRAFTED WITH HUMAN SYNOVIUM TISSUE

This is a continuation-in-part of application Ser. No. 07/669,428, filed Mar. 15, 1991, the entire contents of which are incorporated herein by reference.

BACKGROUND OF THE INVENTION

1. Technical Field

The present invention relates, in general, to severe combined immunodeficiency disease (SCID) mice and, in particular, to SCID mice engrafted with synovium and the methods of using same.

2. Background Information

Rheumatoid arthritis (RA) and other forms of inflammatory synovitis are debilitating autoimmune diseases. In RA, immune cells (T cells, B cells, monocytes) home to synovial tissues, and there mediate synovial inflammation that eventually leads to joint destruction. Treatments for RA and other types of inflammatory synovitis are only symptomatic and in general do not prevent joint damage. While animal models of animal synovitis exist, these models differ in many aspects from human RA. Currently, there is no animal model of human RA. An ideal in vivo model of human synovitis would include human synovium, yet be readily available in an animal host for study under controlled conditions using pharmacologic agents to induce or inhibit the synovial inflammatory process.

In 1988, McCune and colleagues described a system in which human fetal thymic and fetal liver grafts grew in C.G-17 scid/scid (SCID) mice (McCune et al (1988) *Science* 241:1632). Adams et al. recently reported that synovium could engraft under the renal capsule of SCID mice but these authors were unable to characterize the grafts or to repeatedly successfully engraft SCID mice with synovium due to sepsis in engrafted animals and recipient death ((Abstract) 54th Meeting American College of Rheumatology, Seattle, Washington, Oct. 27–Nov. 1, 1990).

Applicants have engrafted synovium under the renal capsule of SCID mice, characterized the inflammatory mediators present, and determined the techniques necessary to successfully engraft >90% of animals with synovium (Rendt et al (Abstract) Keystone Symposium, Lake Tahoe, Calif., March 15–21, 1991; Rendt et al *Fed. Proc.* 1991). Applicants have observed that human synovial tissue grows well in SCID mice, but after 6–10 weeks frequently contains fewer inflammatory cells than the original engrafted tissue. To determine if human T cells can migrate to human synovial grafts in SCID mice, autologous or allogeneic T cells were injected into the peritoneal cavity of SCID mice engrafted with human synovium. After 7 days in vivo, PB human T cells were isolated from grafts, expanded in vitro, and their TCR vβ gene usage determined. Unexpectantly, the only other site in which human PB T cells were found 7 days after IP injection was SCID mouse lymph nodes.

Accordingly, the present invention relates, at least in part, to methods of using immunodeficient SCID mice to grow human synovial explants as xenografts. The SCID mice containing the viable human synovial xenografts constitute an in vitro animal model of human synovial disease. This animal model can be used to facilitate the development of new drugs for treatment of RA, and provides a powerful in vivo model with which to study the pathogenesis of RA.

SUMMARY OF THE INVENTION

It is the general object of this invention to provide a mouse containing synovial xenografts.

It is a specific object of the invention to provide an immune deficient scid/scid mouse containing a mammalian synovial xenograft.

It is another object of the invention to provide a method of screening anti-inflammatory and immunosuppressive drugs for efficacy and toxicity on mammalian tissue.

It is another object of the invention to provide a system for screening human tissue for human pathogens that also grow in mice (e.g. lyme arthritis etiologic agent *Borrelia burgdofei*).

It is yet another object of the present invention to provide for the identification of T cell receptor types in T cells that are capable of migrating to synovium and/or lymph node tissue.

Further objects and advantages will become clear from the description that follows.

Black arrowhead indicates multinucleated giant cell; white arrows indicate type A synovial lining cells. Panel c shows synovial graft 21-2 six weeks after implantation of fresh synovium 21. Arrows indicate borders of the graft. White bar=1 mm. Panel d shows an H and E-stained section of synovial xenograft 21-4, six weeks after implantation of synovium 21 (×100). Graft is overlying the renal parenchyma, with the dotted line indicating the graft-kidney interface. Arrows indicate the renal capsule; rt indicates renal tubules. Panel e shows an H and E-stained section of synovial xenograft 21-8 six weeks after implantation of synovium 21 (×400). Graft 21-8 appears above renal parenchyma, separated by the dotted line. Large arrowheads indicate pigmented macrophages, small arrows indicate non-pigmented macrophages; rt denotes renal tubules. Panel f shows an H and E-stained section of the same specimen (×400). Arrowhead indicates a multinucleated giant cell.

Figure 4:
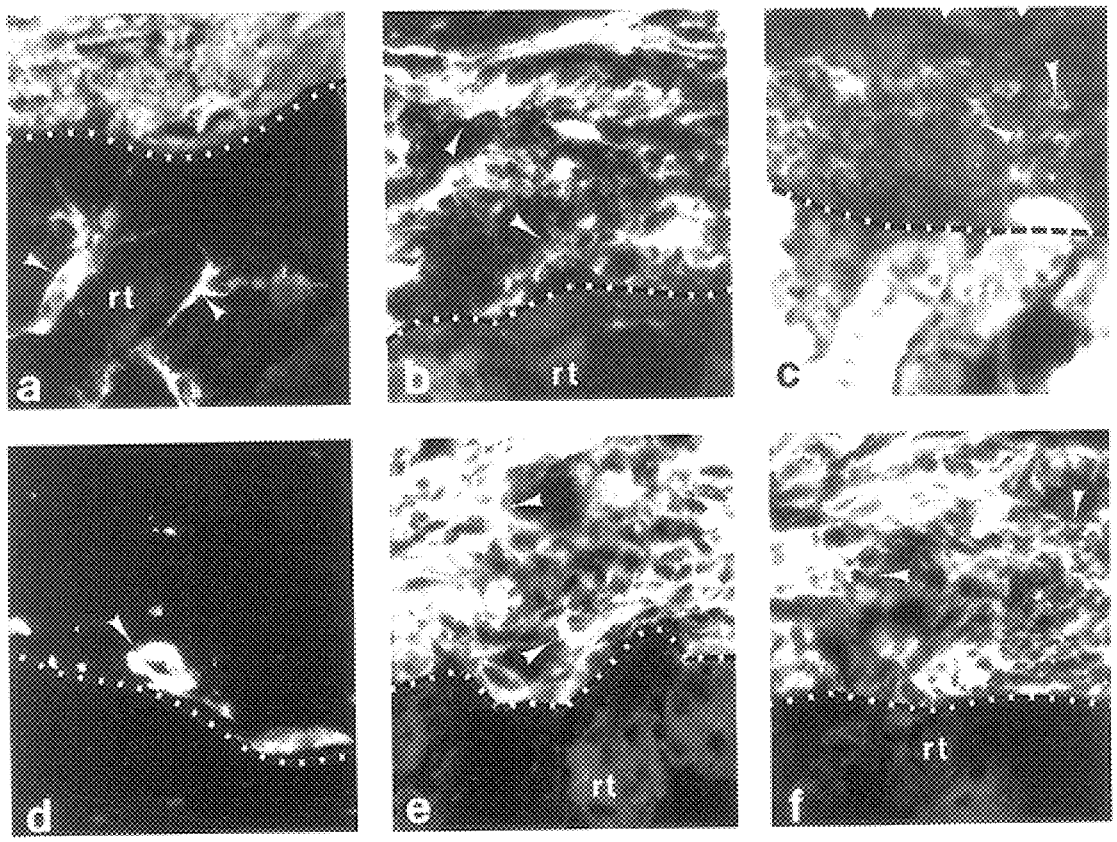

FIGS. 4(A–F): Phenotypic Analysis using Indirect IF of JRA Synovium (No. 21). Engrafted in SCID mice. In all photographs, the graft is seen at the top, overlying the renal parenchyma, with the dotted line showing the graft-kidney interface; rt indicates renal tubule. In Panel a, TE7+ fibroblasts (arrowheads) are shown invading the renal parenchyma. In Panel b, Mol+ macrophages (arrowheads) are seen within the graft. Panel c shows CD7+ T lymphocytes (arrowheads). White triangles show the renal capsule overlying the graft. Panel d contains a V2+ human vessel (arrow). Panel e shows graft HLA Class I expression (arrowheads) and Panel f shows graft HLA Class II expression (arrowheads) (all panels, ×400).

Figure 5:
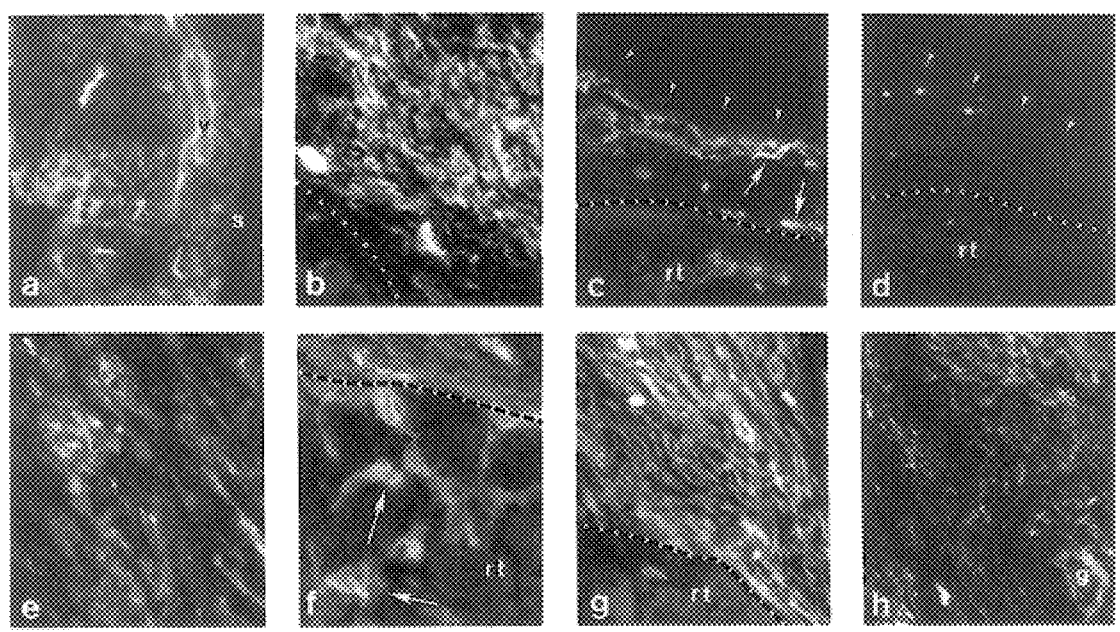

FIGS. 5(A–H): Expression of Adhesion Molecules by Engrafted Human Synovium in SCID Mice. In Panels b, c, d, f, g, and h, the graft is seen overlying the renal parenchyma, with the dotted line showing the graft-kidney interface; rt indicates renal tubules. Panel a shows fresh synovium no. 21 with diffuse expression of ICAM-1 on mononuclear cells and vessels (v) indicates synovial type A lining cells. In Panel b, diffuse expression of ICAM-1 is seen throughout graft 21-4, six weeks after implantation of JRA synovium no. 21. Panels c and d show sequential sections of the same area of graft 28-4 five weeks after implantation of normal synovium no. 28. Panel c shows multiple V2+ human blood vessels (arrows), and Panel d, reacted with ICAM-1, shows that the same blood vessels are ICAM-1. Small arrowheads outline the renal capsule overlying the graft. In Panel e, diffuse expression of LFA-1 is seen in the graft 21-8, six weeks after implantation of JRA synovium no. 21. In Panel f, CD44 is expressed on fibroblasts and vessels in graft 21-8, with CD44+ fibroblasts invading the renal parenchyma (arrows). In Panel g, diffuse expression of CD29 (VLA-β) is seen in graft 21-4, six weeks after implantation of JRA synovium no. 21. Panel h shows diffuse expression of LFA-3 in graft 21-4, six weeks after implantation of JRA synovium 21; g indicates multinucleated giant cell within graft, (all panels ×400).

Figure 6:
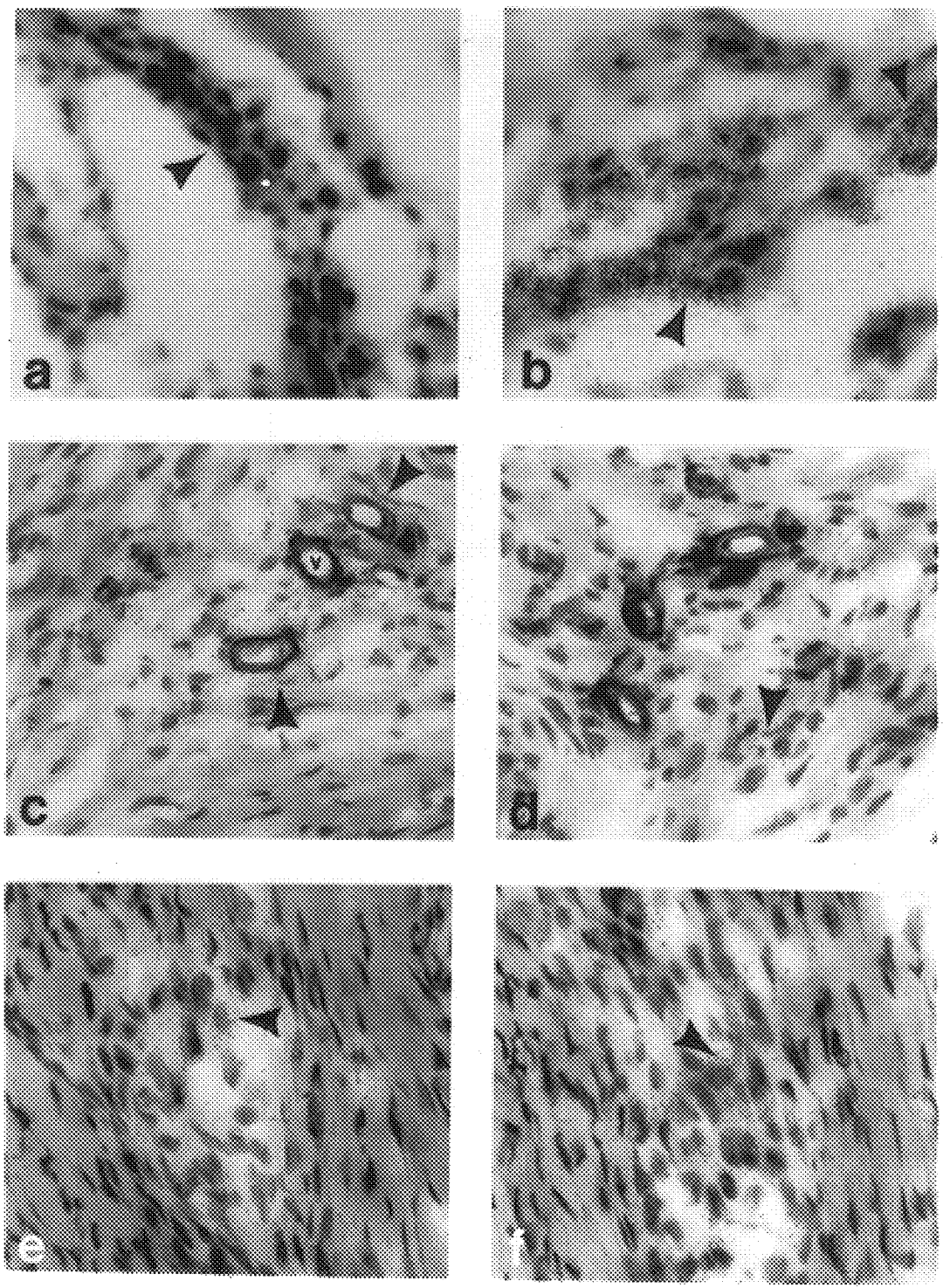

FIGS. 6(A–F): Demonstration of Gelatinase and TIMP mRNA expression by fresh RA synovium and by RA and JRA Synovial Grafts in SCID Mice. Synovium 293 is shown in Panels a and b, grafts 27-7 in Panels c and d, and graft 21-6 in Panels e and f. TIMP mRNA expression is shown in the first photograph of each pair, while gelatinase mRNA expression is shown in the second. Panel a shows synovium 293, H and E stain, ×400. Arrowhead indicates Type A synovial lining cell, and silver particles identifying cells with TIMP mRNA expression are seen throughout the synovium. Panel b shows synovium 293, H and E stain (×400). Arrowheads indicate silver granules marking site of gelatinase mRNA expression. Panel c shows grafts 27-7, H and E stain (×400). Arrowheads show silver granules indicative of TIMP mRNA expression. V indicates one of the three vessels seen in this section. Panel d shows a sequential section of the same tissue as Panel c, with arrow indicating gelatinase mRNA expression. Panel a shows graft 21-6, H and E stain (×400). Arrowhead shows silver granules indicative of TIMP mRNA expression. Panel f shows the same specimen, with arrowhead indicating gelatinase mRNA expression.

Figure 7:
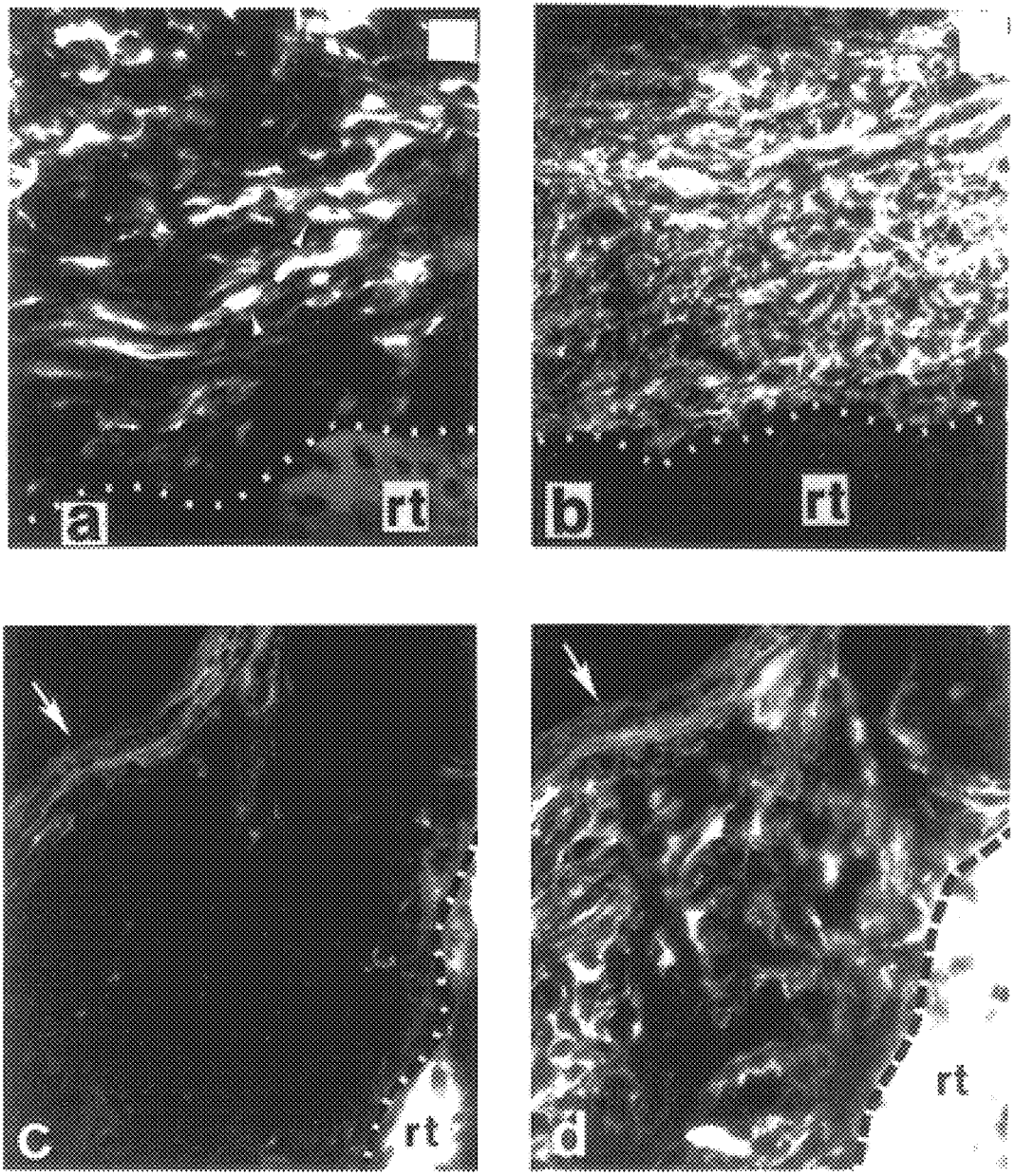

FIGS. 7(A–D): Analysis of the Effects of Human Synovial Graft Transferrin Receptor in Animals Treated with IP Hydrocortisone. Panels a and b show representative grafts from experiment 21 stained with mAbs to transferrin receptor (Panel a, Graft 21-4) and fibronectin (Panel b, Graft 21-2). Widespread expression of both these markers is evident. Panels c and d show sequential sections of graft 27-8, from a SCID mouse that received IP hydrocortisone. In Panel c, no transferrin receptor expression is seen, while fibronectin expression persists (Panel d). Arrows indicate overlying renal capsule. Dotted line indicates graft-kidney interface; rt indicates renal tubules (all panels, ×400).

Figure 8:
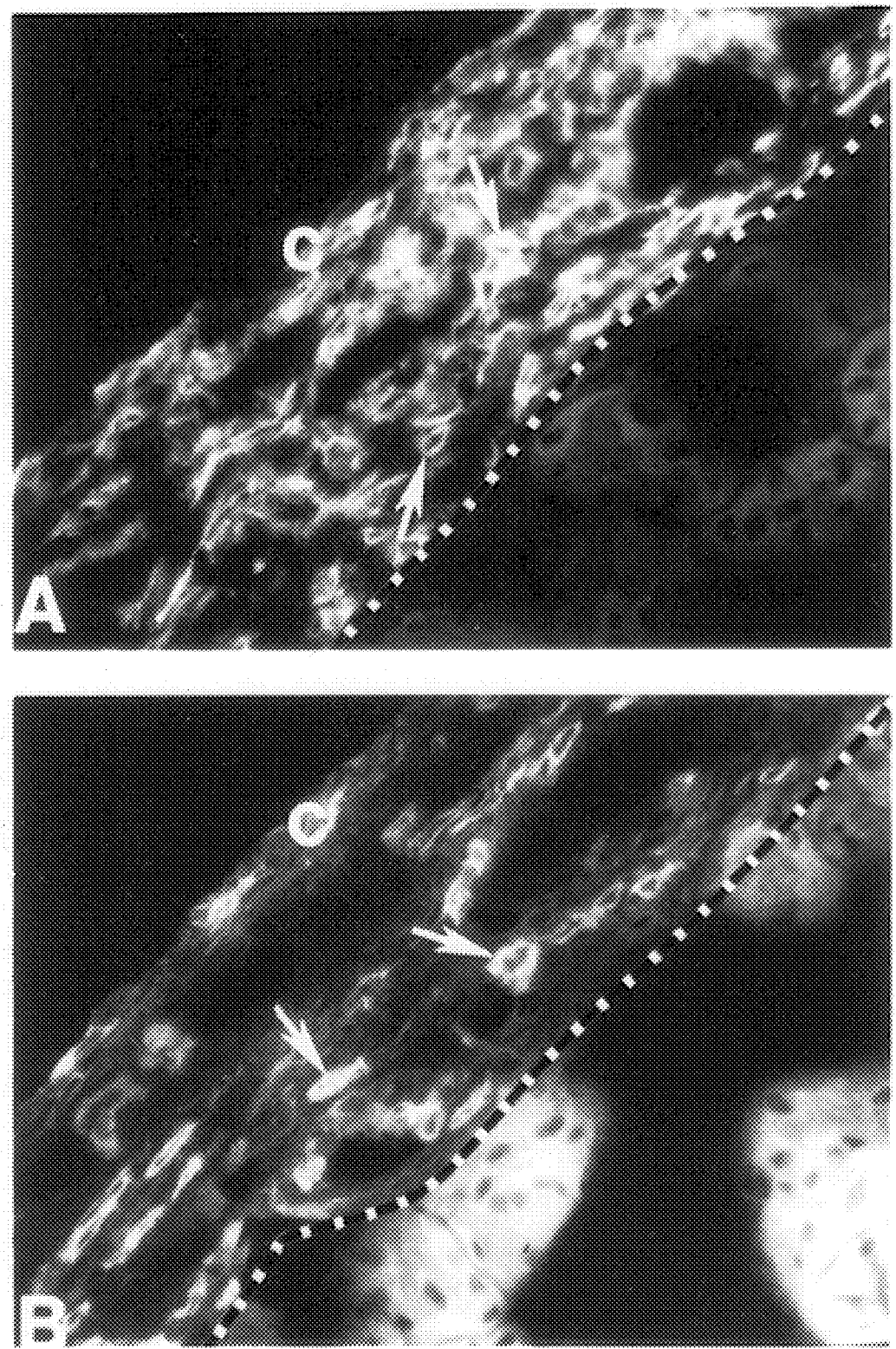

FIGS. 8(A–B): Demonstration of HLA B27+ Cells which have Migrated after IP Injection to HLA B27-Synovial Grafts. In both panels, the RA synovial graft is seen to the left, and the kidney parenchyma is seen to the right, with the graft-kidney interface indicated by a dotted line. Panel a shows RA synovial graft no. 29-9 (HLA B27-) with arrowheads indicating HLA B27+ T cells; c indicates the renal capsule. Panel b shows the same graft stained with mAb Leu 4, demonstrating numerous CD3ε+ cells within the graft (arrows), but not in the kidney parenchyma. c indicates the renal capsule (both panels, ×400).

Figure 9:
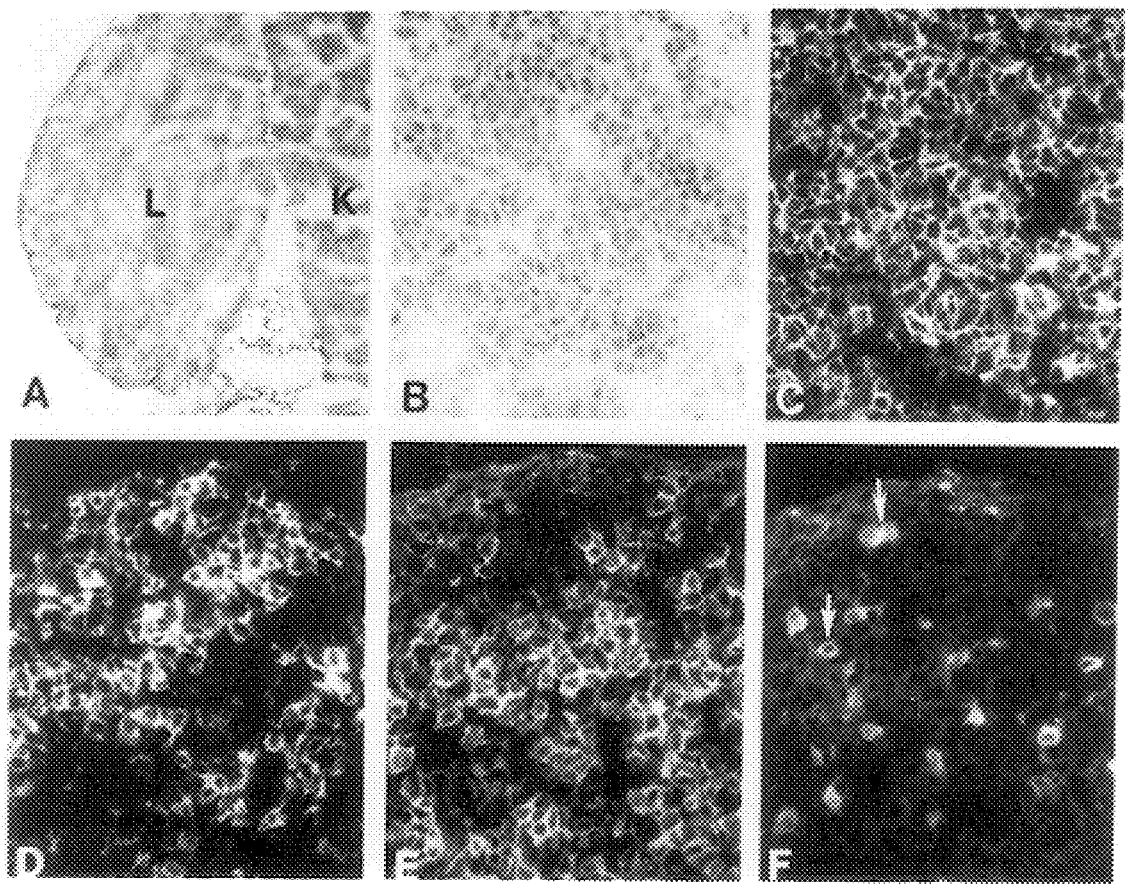

FIGS. 9(A–F): Phenotypic Analysis of Human Cells Present in a Murine Pararenal Lymph Node. Panel a shows a low power (×100) view of the lymph node (L) adjacent to SCID mouse 29-4 kidney(K). Panel b shows a higher power (×400) view of the lymph node, showing mononuclear cells. In panel c, human HLA B27+ cells are seen. In panel d, expression of human CD44 is seen on cells within the lymph node. In panel e, numerous human CD3ε+ cells are seen within the lymph node. In panel f, arrows indicate scattered OT145 (TCR Vβ6.7)+ cells within the lymph node.

Figure 10:
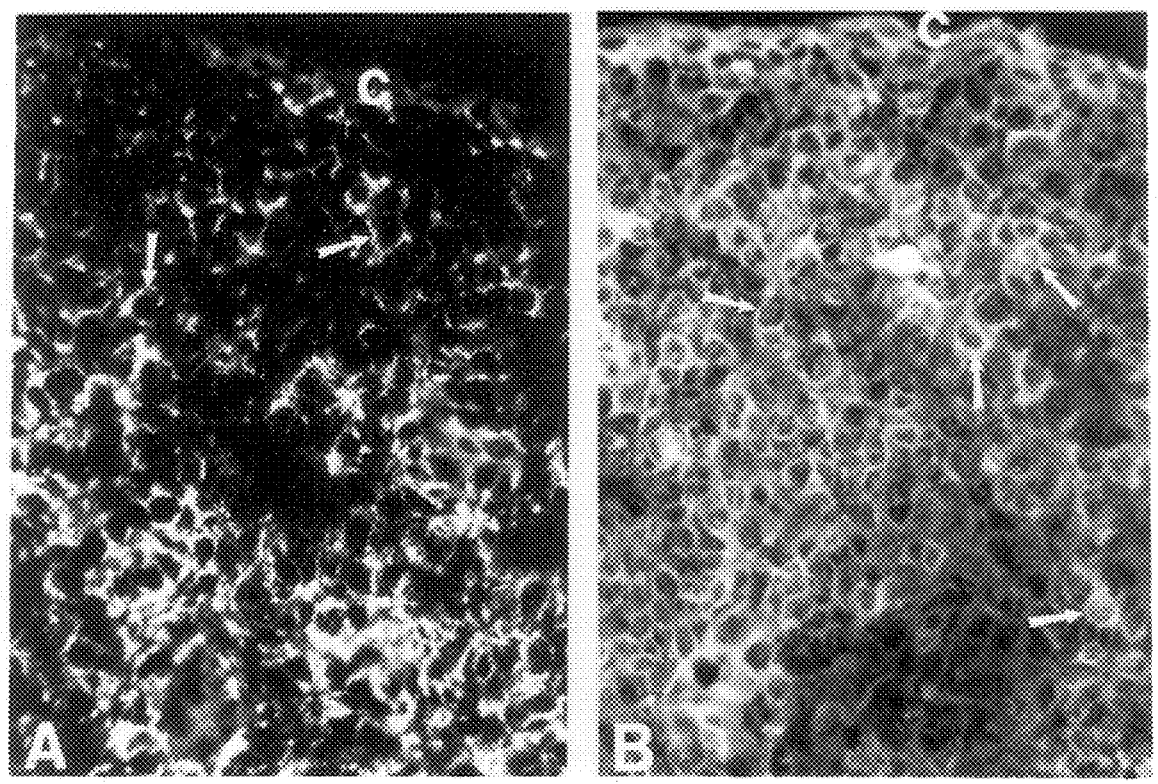
Figure 11A:
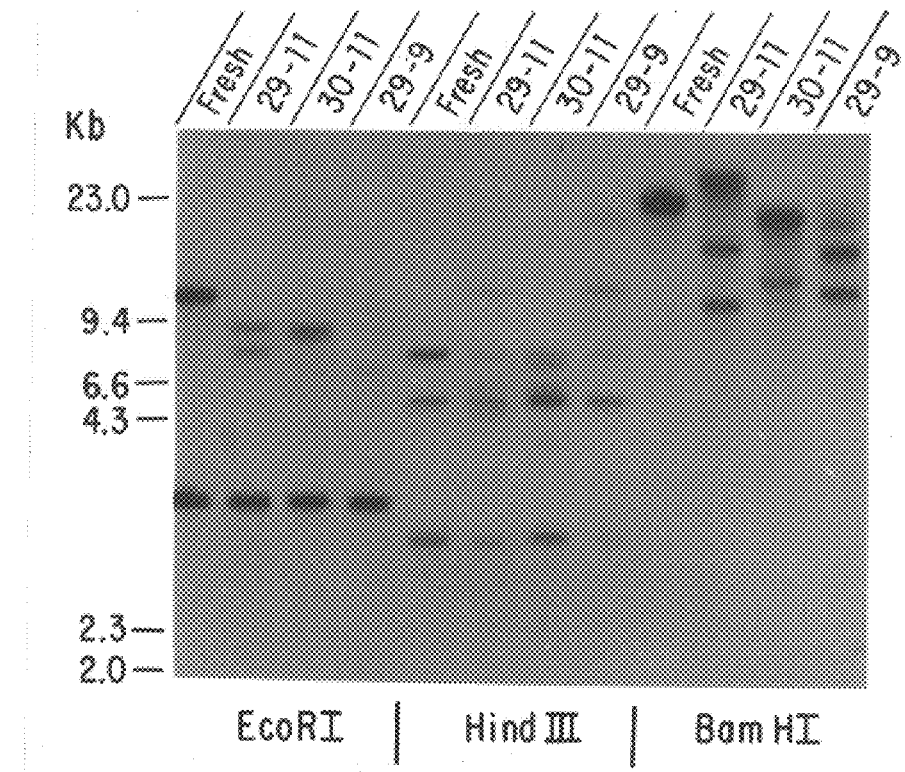
Figure 11B:
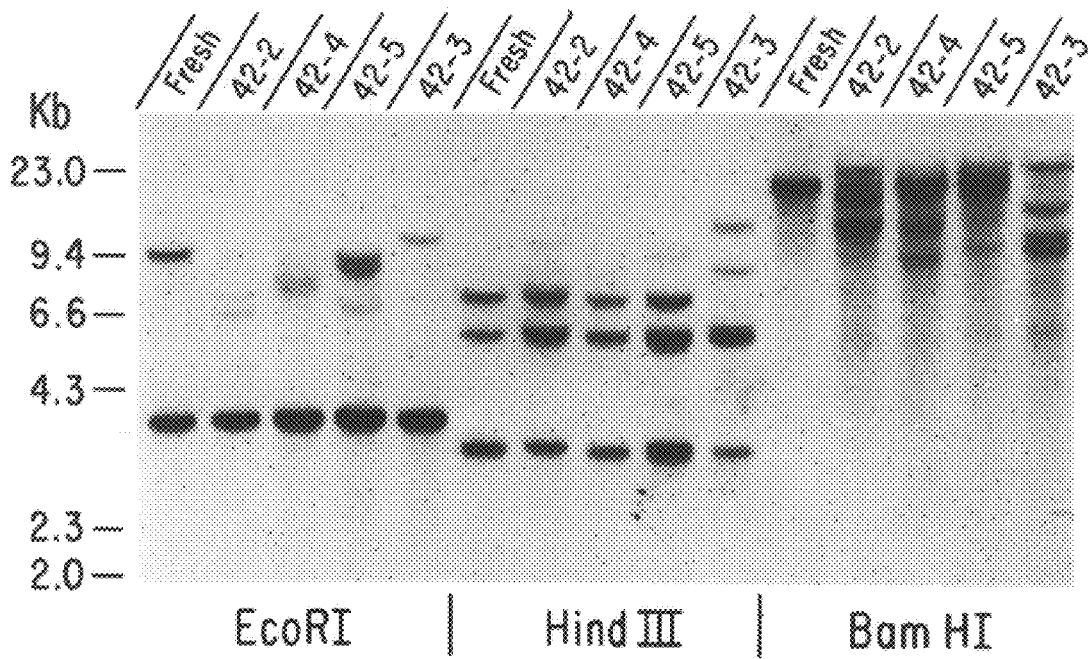
Figure 11C:
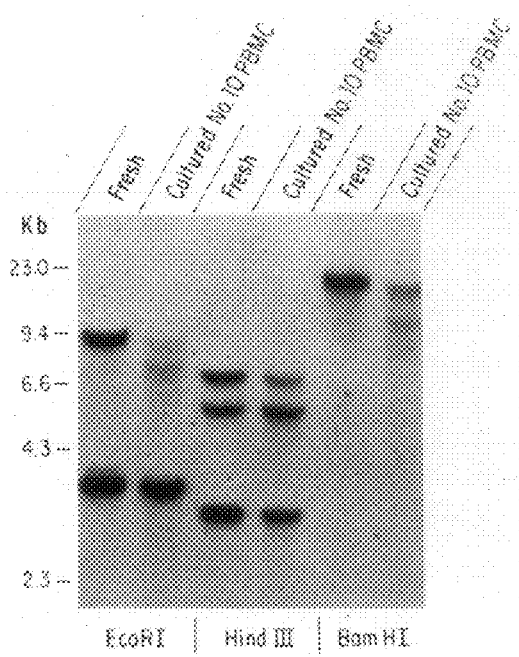
Figure 11D:
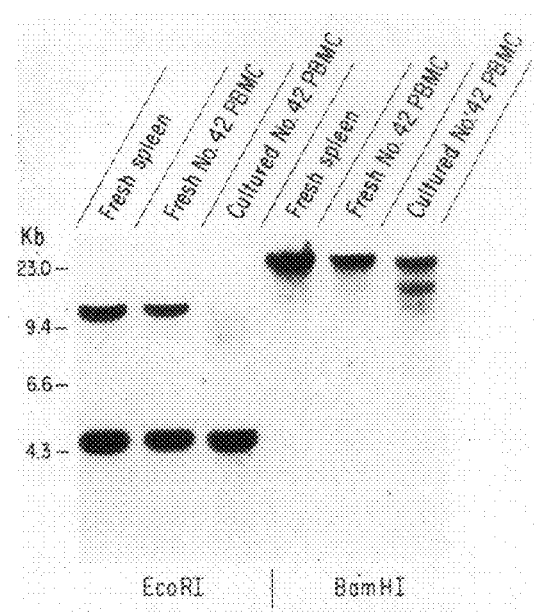

FIGS. 10(A–B): Phenotypic demonstration of human T cells in a murine lymph node. Panels a and b are high power (×400) views of a pararenal lymph node from SCID mouse 29-4. c indicates lymph node capsule. Panel a shows LN stroma reactivity with mAb 34-4-21S, directed against murine HLA $D_d$ (arrows). In panel b, βF1+ human T cells (arrows) are seen.

FIGS. 11(A–D): Southern blot analysis of oligoclonal human T cells grown from human synovial grafts in SCID mice. Panel a shows the analysis of fresh normal donor no. 10 PBMC and the three grafts from animals containing RA synovium no. 29 (grafts 29-11, 29-9) and no. 30 (graft 20-11) from which T cells were grown. DNA was extracted and digested with EcoRI, BamHI, or HindIII restriction endonucleases, and the DNA probed with cDNA for the Cβ p region of TCRβ. Fresh T cells from normal donor no. 10 did not show clonal TCRβ gene rearrangements, while T cells grown in vitro from 29-11, 30-11, and 29-9 did show TCRβ gene rearrangements in oligonoclonal patterns with each of the restriction enzymes tested. Panel b shows a similar analysis performed on fresh spleen DNA as a control, and on DNA from grafts from animal containing B27+ spondyloarthropathy synovium no. 42. Animals 42-2, 42-3, and 42-4 received an IP injection of normal no. 10 PBMC, while 42-5 received an IP injection of autologous no. 42

PBMC. HLA typing of the cultured T cells from 42-2, 42-3, and 42-4 grafts verified their identity as cells from normal donor no. 10. Fresh spleen DNA as a control did not show clonal TCRβ gene rearrangements, while cultured autologous and allogeneic T cells from the spondyloarthropathy grafts 42-2, 42-3, 42-4, and 42-5 did show TCRβ gene rearrangements in oligoclonal patterns. Panels C and D show that compared to control uncultured PBMC DNA, DNA from day 14 cultured normal no. 10 and no. 42 PBMC (never having been injected into SCID mice) also demonstrated oligoclonal TCRβ bands.

Figure 12A:
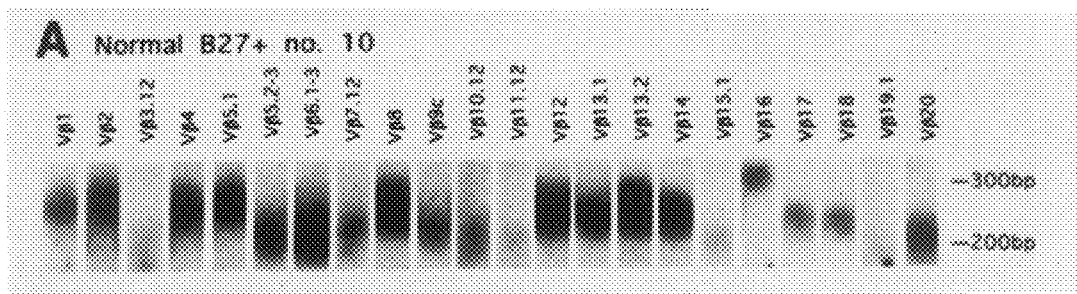
Figure 12B:
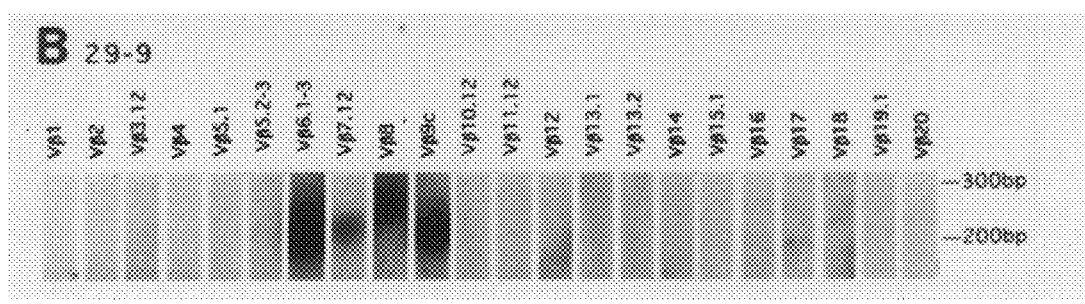
Figure 12C:
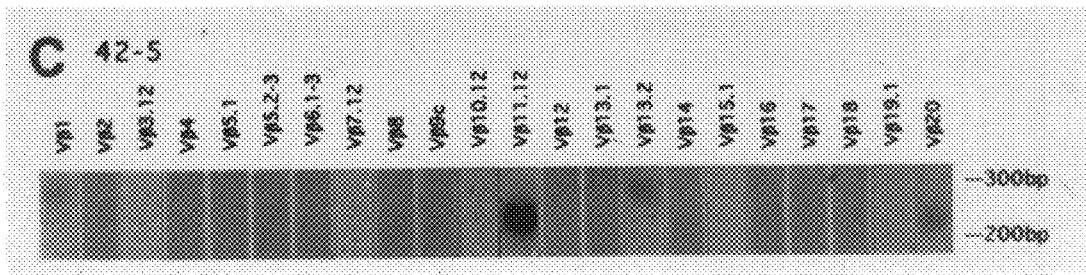

FIGS. 12(A–D): TCR VP analysis of T cell mRNA expression in human PB T cells grown from synovial xenografts in SCID mice. Panels a, b, and c show TCR Vβ types present by Southern blot analysis of PCR-reverse transcribed and amplified Vβ mRNA from normal fresh PB T cells (Panel a), from T cells grown from graft no. 29-9 (Panel b), and from T cells grown from graft 42-5 (Panel c). Panel d shows a summary of all of the TCR Vβ analyses performed on T cells grown from synovial xenografts in SCID mice as well as from control T cells grown in vitro.

DETAILED DESCRIPTION OF THE INVENTION

The present invention results, at least in part, from Applicants' demonstration that both normal and inflammatory human synovial tissue grow as xenografts in SCID mice, and further, that autologous and allogeneic PBT cells injected IP into engrafted SCID mice selectively migrated to synovial grafts and to SCID mouse lymph nodes. The rate of engraftment is high (~100%) regardless of whether an immunosuppressive regimen is used. This result contrasts with previous reports that while human PB mononuclear cells readily engraft in SCID mice, postnatal tissues, such as thymus, require concomitant immunosuppressive treatment to enhance graft survival from about 30% in untreated animals to about 70%.

Synovial tissue, normal or inflammatory, grown as a xenograft in SCID mouse provides a much needed model for human synovial inflammatory disease. This model is reflective of the pathophysiologic process of human synovitis in vivo, is susceptible to pharmacologic modification of the disease process and is readily generated with a reproductively high rate of engraftment. One skilled in the art will appreciate that the ability to modify the inflammatory process in engrafted human synovium by treatment of the SCID mouse host with anti-inflammatory drugs provides an extremely useful model for screening new agents for potential anti-inflammatory activity.

The data presented in the Examples that follow indicate that human synovium engrafted into SCID mice is useful for reflecting pathological events in synovitis and for studying pharmacologic modification of inflammation. Human synovium from JRA and RA patients engrafted in SCID mice show many of the characteristics of the preimplantation synovium. These characteristics include macrophage infiltration and syncytial giant cell formation, foci of lymphocytes, fibroblast proliferation, calcification, and production of gelatinase. The lack of graft expression of collagenase and stromelysin mRNA and the presence of mRNA for TIMP an gelatinase in grafts indicate that: 1) there may be different factors in synovial grafts regulating TIMP and gelatinase versus collagenase and stromelysin, and 2) the engrafted synovial micro- environment might be shifted more to an "anti-inflammatory" state (higher levels of TIMP compared to proteases) compared to the fresh synovium from which the grafts were derived. In view of the presence of extraordinary calcification in certain of the RA, but not normal, grafts, an important model for tissue calcification in vivo would appear also now to be provided.

Injection of $10 \times 10^6$ peripheral blood mononuclear cells from an HLA B27 positive normal human into the peritoneal cavity of a SCID mouse into which a HLA B27 negative RA synovium had previously been engrafted demonstrated that 7 days after injection of B27+ peripheral blood mononuclear cells, numerous human B27+ cells were found to have homed to the human B27– synovial graft located under the renal capsule of the SCID mouse. These data demonstrated the feasibility of inducing further T cell mediated immune responses in engrafted synovium.

Applicants' results relating to the proinflammatory events in the human synovial xenograft model indicate that the degree of fibroblast proliferation as measured by fibroblast transferrin receptor expression is downregulated by in vivo corticosteroids. Accordingly, it is anticipated that this model will be useful to study in vivo effects of pharmacologic agents on human synovial T, B and macrophage function, and to use this model as reflective of inflammation in tissues in general.

One skilled in the art will appreciate that synovial tissue engraftment in SCID mice is an ideal system in which to study the sequence of events in which certain populations of lymphocytes and monocytes enter the synovial microenvironment. Human synovial xenografts in SCID mice are well vascularized, and both human and murine vessels are present. The data presented in the following Examples indicate that the animal model disclosed herein is valuable for study of immunopathologic mechanisms of inflammatory synovitis and for testing of anti-inflammatory pharmacologic agents in vivo on human synovial tissue.

One skilled in the art will appreciate from the following non-limiting Examples that both autologous and allogeneic PB T cells injected IP can selectively migrate to human synovial xenografts and to murine lymph nodes and that T cell migration into xenografts in SCID mice will be useful for identifying pathogenic clones of T cells in allograft rejection and in inflammatory synovitis. Study of the migration of RA PB and synovial T cells to autologous synovial grafts with comparison of fresh synovial Vβ types compared with homed IP-injected T cell Vβ types in synovial xenografts can be expected to be of help in evaluating this issue. The ability to demonstrate selective migration of allogenic and autologous T cells to xenografts and to murine LN is evidence of the usefulness of the SCID mouse model to study human T cell homing.

EXAMPLES

The following protocols and experimental details are referenced in the Examples that follow.

Animals

SCID mice (male and female, 5–6 weeks of age) were raised under pathogen-free conditions in the barrier facility of the Duke University Vivarium (Barry et al, *J. Exp. Med.* 173:167 (1991)).

Human Synovial Tissue

Human synovium was obtained from 3 patients at the time of joint replacement surgery as discarded tissue from the Department of Pathology, Duke University (Haynes et al, *Arthritis Rheum.* 31:947 (1988)). Patient 21 was a 62 year old female with juvenile RA for 47 years; medication use at the time of total hip replacement was oral aspirin 325 mg, three per day. Patient 27 was a 62 year old male with deforming RA for 13 years. Medications prior to total knee replacement included methotrexate 15 mg/week, aspirin 1625 mg 4 times daily, naproxen 375 mg twice daily, and folic acid 1 mg twice weekly. Patient no. 28 was a 69 year old female on no regular anti-inflammatory medications, who underwent corrective surgery for left hallux valgus and dorsal subluxations of her left second and third metatarsophalangeal joints. Patient no. 29 was a 70 year old native American Indian female with a 35 year history of deforming RA on NSAID at the time of her right total hip replacement. Patient no. 30 was a 52 year old white female with a 35 year history of RA whose treatment at the time of bilateral total knee replacements was acetaminophen and codeine. Patient no. 42 was a 54 year old white male with HLA-B27-related spondyloarthropathy treated with prednisone 5 mg/d and sulfasalazine 1 g three time daily at the time of his left wrist fusion. Synovium no. 28 was used as normal, non-inflammatory synovium. Synovial tissue samples were cut into 3 mm$^3$ pieces, frozen in 7.5%DMSO, 15% fetal bovine serum, and stored in liquid nitrogen until use.

Transplantation of Human Synovium in SCID Mice

For engraftment of human synovium under the renal capsule of SCID mice, general anesthesia and surgical implantation of the tissue was performed. (Barry et al, *J. Exp. Med.* 173:167 (1991)).

At the time of autopsy, spleen, liver, thymus, and engrafted kidney were removed and snap frozen in a dry ice/ethanol slurry and stored in liquid nitrogen. Phenotypic analysis of peripheral blood mononuclear cells (PBMC) was performed with mabs directed against human and murine surface lymphocyte markers in direct and indirect immunofluorescence assays and analyzed on a FACS star Plus Fluorescence Activated Cell Sorter (Bectin Dickinson, Mountain View, Calif.). Serum levels of murine immunoglobulins were measured using an ELISA assay for IgM and IgG.

Immunosuppressive Treatment of Engrafted SCID Mice

Mice received either no treatment after surgery, or received IP injections of 25 μl of anti-asialo GM-1 (Wako, Richmond, Va.), every 4–5 days.

Hydrocortisone Treatment of Engrafted SCID Mice

Three SCID mice engrafted with RA Synovium no. 293 received daily IP injections of hydrocortisone sodium succinate 10 mg/kg (Solu-Cortef, Upjohn, Kalamazoo, Mich.), for three days immediately prior to autopsy.

Antibodies

The following anti-human monoclonal antibodies were used: LeuM3 (CD14), Mo-1(CD11b), 3Ale (CD7), Leu 4 (CD3), T4/19Thy5D7 (CD4), Leu 3a (CD4), OKT8 (CD8) (American Type Culture Collection, Rockville, Md.), Leu 2a (CD8), βF1 (anti-TCRβ), WT31 (anti-TCRαβ), TCR-δ1 (anti-TCR-δ), K20 (CD29, VLA-β), TAC (IL2Rα, CD25), 5E9 (CD71 transferrin receptor), FN-15 (fibronectin) (Sigma Chemical Co., St. Louis, Mo.), A3D8 (CD44), B1, B2, 9.1, LFA-3 (CD58), LFA-1, ICAM-1 (CD54, RR-1), 3F10 (anti-HLA class I monomorphic), L243 (anti-HLA DR monomorphic), V2 (anti-human vessels), TE7 (anti-human fibroblasts), CD45-FITC (Bectin Dickinson, Mountain View, Calif.), CD4-PE, CD8-FITC, and CD7-PE (3A1-RD1) (all from Coulter Immunology, Hialeah, Fla.), anti-HLA antibodies against polymorphic HLA determinants 88.2 (DR5), DR7M (DR7), JS-1 (DR3), GS359-13F10 (DR4), 295-3E5 (Qw3), 4AA7 (DQ1+4), 296-8F9 (DQ monomorphic), 8.1 (B8), 295-8DS (B5), 145.2 (B27), 20.1 (A2, Aw69), 192.1 (A9, A32, Bw4), AUF 5.13.7 (A3, A11), 77.1 (Bw6), 348.9F9 (DRw52), 313-9D11 (DRw8+12) (all from Susan Radka, Genetic Systems, Seattle, Wash.), and 4D12 (B5).

Reagents recognizing Vβ types included 42-1C1(Vβ 5) (T Cell Sciences, Inc., Cambridge, Mass., and Dr. Arthur Boylston, St. Mary's Hospital, London, England), OT145 (Vβ6.7) (T Cell Sciences, Inc., Cambridge, Mass. and Dr. David Posnett, Cornell University, N.Y., N.Y.), MX9 (Vβ8), MX11 (Vβ8) (both from Stefan Carrell, Ludwig Institute for Cancer Research, Basel, Switzerland), and S511 (Vβ12) (T Cell Sciences, Cambridge, Mass. and Dr. Robert Bigler, Hahnamman University).

The following antibodies against murine determinants were used: 145-2C11 (CD3ε), H57-597 (anti-TCR-β), CD4-PE (L3T4-PE), CD8-FITC (Lyt2-FITC) (all from Bectin-Dickinson) and Thy-1.2-FITC (J. Kearney, Univ. Alabama, Birmingham, Ala.), CD8 (Lyt-2, Thy-1 (NIMR-1), and mouse macrophage (M1/70.15) (all from Sara-Lab, Accurate Chemicals, Westbury N.Y.), 34-4-21S (anti-H-2 D$^d$), 34-420S (anti-H-2 D$^d$), and MK-D6 (anti-I-A$^d$). Control antibodies included IgGl-FITC, IgG2-PE, (both from Becton-Dickinson) and P3×63/Ag8 ascites. Antibodies were used at saturating concentrations. Control antibodies included IgG1-FITC, IgG2-PE, (both from Bectin-Dickinson) and P3×63/Ag8 ascites.

Immunohistologic Analysis of Tissue Specimens

Tissue samples were embedded in OCT compound (Lab Tek Products, Naperville, Ill.), and serial 4μ sections were cut on a Reischert-Jung Cryostat, model 1800, or an american Optics Cryostat. Sections were mounted on gelatin-coated microscope slides and fixed in acetone (−40° C.) or 5 minutes, and kept at −70° C. prior to use.

Murine anti-human monoclonal antibodies were either directly conjugated, or used in indirect immunofluorescence with a FITC goat anti-mouse IgG (GaM-FITC) (Kirkegaard-Perry, Gaithersburg, Md.). Anti-murine antibodies were either directly conjugated, or used with flouresceinated mouse anti-rat Ig, OX12 (Sera Labs, Accurate Chemicals, Westbury, N.Y.).

In Situ Hybridization on Human Synovial Tissue

In situ hybridization techniques for detection of mRNA for collagenase, stromelysin, gelatinase, and tissue inhibitor of metalloproteases in synovial tissue was performed using known methods.

Allogeneic and Autologous Human PBMC Injection of Engrafted SCID Mice

Seven of 9 mice engrafted with RA synovium no. 29 (HLA B27−) received a single IP injection of allogeneic HLA B27+ human PBMC from clinically normal donor no. 10, either freshly isolated (25×10$^6$ cells or 50×10$^6$ cells/mouse) or after 2 days of concanavalin A (10 μg/ml) (Con A) stimulation (10×10$^6$ cells or 35×10$^6$ cells/mouse) (Table 7). PBMC were administered 1 week prior to autopsy of the mice. Similarly, 8 of the 10 mice engrafted with RA synovium no. 30 (HLA B27−) received a single IP injection of allogeneic HLA B27+ human PBMC from normal donor no. 10, either freshly isolated (25×10$^6$ or 50×10$^6$ cells/mouse) or Con A (10 μg/ml-stimulated (10×10$^6$ or 35×10$^6$ cells/mouse), one week prior to harvest (Table 7). Finally, 6 of the 11 mice engrafted with B27-related spondyloarthropathy synovium no. 42 received a single IP injection of either autologous human PBMC freshly isolated from patient no. 42 (50×10$^6$ cells/mouse) or allogeneic HLA B27+ fresh PBMC from normal donor no. 10 (50×10$^6$ cells/mouse) (Table 1). The remaining mice from each group received no injection of PBMC as controls.

Analysis of Synovial Grafts and Other Murine Tissues

At the time of autopsy, kidneys of mice that had undergone IP injection of autologous or allogeneic human PBMC were placed in a sterile petri dish. Each graft was divided, with half of the graft snap frozen in a dry ice/ethanol slurry, and the other half of the graft placed in tissue culture. Engrafted kidneys as well as spleen, liver, thymus, and appendix were stored in liquid $N_2$ until use. Phenotypic analysis of fresh murine PBMC was performed with mAbs directed against human or murine surface lymphocyte markers in direct and indirect immunofluorescence assays and analyzed on a FACS Star Plus fluorescence activated cell sorter (Becton Dickinson, Mountain View, Calif.).

Cultures of Human T Cells From Synovial Grafts

Of 12 synovial grafts placed in tissue culture, 7 yielded human T cell cultures (Table 1). Graft T cells were expanded with RPMI media supplemented with 15% Human A serum, IL-2 (25 units/ml), PHA (0.5 μg/ml), gentamicin (10 μg/ml), and allogeneic EBV-transformed B cells.

Southern Blot Analysis of DNA Extracted From T Cells Grown From Synovial Grafts

DNA was isolated from cells by digestion with Proteinase K in 50 mM Tris-HCl (pH 7.6), 100 mM NaCl, 1 mM EDTA, and 0.5% SDS. After the cells were incubated at 55° C. for 5–6 hours, the lysate was extracted 2 times with phenol and 3 times with chloroform, and concentrated by precipitation in 1/10 volume of 2 M ammonium acetate and 2.5 volumes of cold ethanol. The DNA was resuspended in 1× TE (100 mM Tris-HCl, 10 mM EDTA). Purified DNA was digested with the appropriate restriction endonucleases as described by the manufacturer, size fractionated on an agarose gel, and transferred to a nitrocellulose filter.

After baking the filters for 1.5 hours at 80° C. under vacuum, blots were hybridized as described using a cloned cDNA probe specific for the human T cell receptor beta chain J and C regions (Yanagi et al, *Proc. Natl. Acad. Sci. USA* 82:3430 (1985); Schanberg et al, *Proc. Natl. Acad. Sci. USA* 88:603 (1991); Toyonaga et al, *Nature* 311:385 (1984)). Blots were dried and exposed to Kodak-X-O-Mat film at −70° C. with Dupont Cronex Lightning-plus intensifying screens.

Polymerase Chain Reaction (PCR) Analysis of TCR Vβ mRNA Extracted from T Cells Grown From Synovial Grafts Total cellular RNA was isolated by a modification of a standard guanidinium thiocyanate extraction followed by cesium chloride ultracentrifugation (Sambrook et al, in Molecular Cloning: A Laboratory Manual. 2nd edition (1989) Cold Spring Harbor Laboratory Press, Cold Spring Harbor, Mass.). RNA samples were redissolved in $H_2O$ and quantitated by determining absorbance at 260 nm.

To synthesize cDNA, 2 μg of total RNA was incubated at 42° C. for 1 hr in a 20 μl reaction mixture containing 1 μg Oligo d(T) 12–18 (Pharmacia, Madison, Wis.), 1 mM each dNTP, 20 U human placental ribonuclease inhibitor (Promega, Piscataway, N.J.), and 30 U avian myeloblastosis virus reverse transcriptase (Stratagene, La Jolla, Calif.) in 50 mM Tris-HCl, pH 8.3, 20 mM KCl, 10 mM $MgCl_2$ and 50 mM dithiothreitol. After incubation, the reaction mixture was heated to 70° C. for 10 min to inactivate the reverse transcriptase and stored at −20° C. for later PCR amplification. Mock reverse transcription reactions were performed without reverse transcriptase to control for DNA contamination in PCR analysis.

Oligonucleotides were synthesized using nucleoside cyanoethylphosphoramidite chemistry on an ABI 380B DNA synthesizer. Further purification of oligonucleotides was performed by extracting once with phenol:chloroform:isoamyl alcohol (25:24:1) and once with chloroform (Sambrook et al (1989) in Molecular Cloning: A Laboratory Manual. 2nd edition (1989) Cold Spring Harbor Laboratory Press, Cold Spring Harbor, Mass.). The oligonucleotides were ethanol precipitated as above and quantitated spectrophotometrically. Absorbance unit values (μg/O.D.) were determined by calculating EMMW for each oligonucleotide; EM=(16000×A)+(12000×G)+(7000×C)+(9600×T) and MW=(312.2×A)+(328.2×G)+(288.2×C)+(303.2×T−61.

For polymerase chain reaction amplification of Vβ cDNA's, a master mix containing cDNA (100 ng RNA equivalents per PCR reaction), 200 μM of each dNTP, and 2 μM of common 3'Cβ oligonucleotide was prepared in Taq reaction buffer: 10 mM Tris-HCl, pH 8.3, 50 mM KCl, 1.5 mM $MgCl_2$, and 0.01% (w/v) gelatin. Taq polymerase (Stratagene, La Jolla, Calif.) was added to the master reaction mixture at concentration of 2.5 U per reaction. The mixture was vortexed vigorously, and aliquoted into separate GeneAmp Tubes (Perkin Elmer/Cetus, Norwalk, Conn.), each containing 1 μl of a different 5'Vβ region specific oligonucleotide primer at 2 μM concentration. Each reaction tube was overlaid with 50 μl of mineral oil and subjected to 21 amplification cycles using a Perkin Elmer/Cetus thermocycler as follows: initial denaturation of 3 min at 94° C., followed by cycles of 94° C., 55° C., and 72° C., each for one min. A 10 μl sample of each amplification reaction was loaded in a 4% agarose gel [3% wide range agarose (Sigma, St. Louis, Mo.) & 1% regular agarose (IBI, New Haven, Conn.)] and run for 2.5 h at 100 V. Due to the low number of cycles, ethidium bromide-stained bands were not always visualized. The sequences of the oligonucleotide primers used for Vβ amplification have been previously described (Wucherpfennig et al, *Science* 248:1016 (1990); Choi et al, *Proc. Natl. Acad. Sci. USA* 86:8941 (1989); Hall et al, *Biotechniques*. In press.). The size of amplified cDNA products ranged from 190 to 310 base pairs using a common 3'Cβ oligonucleotide primer homologous to both Cβ1 and Cβ2.

In concert with TCR Vβ panel analysis, oligonucleotide primers, CD7-3 (5'ACAACCTGACTATCACCATG'3) (SEQ ID No:1) and CD7-4 (5'CGAGCATCTGTGCCATCCTT'3) (SEQ ID No:2) specific for the T cell specific CD7 gene were used as positive controls for reverse transcription PCR reactions, and as a control to detect DNA contamination in RNA samples. CD7-3 and CD7-4 amplify a region of the CD7 gene between exon 2 and exon 3 which allows discrimination of genomic DNA from amplified cDNA by presence of 300 bp intron.

To detect specific PCR amplified Vβ region specific gene products, PCr products were size fractioned by agarose gel electrophoresis, transferred to Duralon-UV nylon membranes (Stratagene, La Jolla, Calif.) under alkaline conditions, and immobilized by UV irradiation using a Stratagene Stratalinker, according to manufacturer's specifications, and by baking in a vacuum oven at 80° C. for 90 min. Membranes were incubated for 5 min in 6× SSC (1× SSC=0.15 M NaCl, 0.013 M sodium citrate) and prehybridized in 6× SSC, 5× Denhardt's solution, 0.5% SDS, and 100 μg/ml denatured herring sperm DNA, for 2 h, at 55° C. Hybridization was carried out for 14–16 h at 55° C., in a solution of 6× SSC, 0.5% SDS, and 100 μg/ml denatured herring sperm DNA with [$^{32}$P]-5'end-labeled CβN, a nested oligonucleotide (5'TGTTCCCACCCGAGGTCGCT'3) (SEQ ID NO: 3). CβN was labeled with [$^{32}$P]ATP (>5,000 Ci/mmol, Amersham, Arlington Heights, Ill.) by T4 polynucleotide kinase (IBI, New Haven, Conn.) as follows: incubation of 10 pmol CβN in 0.5 M Tris-HCl, pH 8.0, 0.1 M MgCl2, 50 mM spermidine, and 50 mM dithiothreitol, at 30° C. for 1 h followed by heat inactivation of kinase at 70° C. for 10 minutes. Unincorporated ATP was removed by spun column chromatography using a 1 cc Sephadex G-25 (Sigma, St. Louis, Mo.) syringe column. Southern blots were washed two times in 6× SSC and 0.1% SCS at room temperature for 15 min followed by stringent washing in 6× SSC and 0.5% SDS at 60° C. for 1 min, 20° C. below mean stacking temperature of a nested oligonucleotide, CβN. The membranes were exposed to Kodak X-OMAT X ray film at −70° C.

Determination of the Lower Limit of Detection of Select TCR Vβ Types in T Cell Suspensions To determine the sensitivity of the PCR-based Vβ panel analysis, reverse transcription of equivalent amounts of RNA from two T cell clones, CEM-T (Vβ 9.1) and HPB-ALL (Vβ 5.3) was performed. cDNA from CEM-T and HPB-ALL was intermixed creating titration gradients of each Vβ target from 0.5% to 99.5%. 100 ng RNA equivalents of the intermixed cDNA's were amplified by PCR as described above using Vβ oligonucleotides specific for each Vβ target. PCR products were then separated by gel electrophoresis, transferred to nylon membranes, and hybridized with the nested primer, CβN, as described above. Vβ9.1 and Vβ5.3 specific signals were detected when 0.5% of either T cell type was present.

Example 1

Engraftment of Human Synovium into SCID Mice

To optimize xenograft growth, the rate of engraftment of human synovium in SCID mice treated with anti-asialo GM-1 antiserum was initially compared versus SCID mice receiving no immunosuppressive treatment. For engraftment of human thymus tissue in SCID mice, treatment of transplanted animals every 4–5 days IP with anti-asialo GM-1 anti-serum markedly facilitated engraftment. In contrast to thymus tissue, it was found that human synovium engrafted in SCID mice equally well in anti-asialo GM-1 treated and untreated SCID mice in only 37% of animals (11), normal, JRA and RA synovial tissues all engrafted in 100% (12 of 12) of untreated animals (Table 1). All of the 21 animals engrafted were SCID Ig− before surgery as determined by ELISA for serum IgG and IgM levels. After 5 to 9 weeks, at the time of sacrifice, 2 animals (no. 21.7, 27-6) were found to be SCID Ig+; neither received anti-asialo GM1. Although thymus tissue engrafted in untreated SCID mice in only 37% of animals (11), normal and inflammatory synovial tissues engrafted in 95% (40 of 42) of untreated animals and in 89% (8 of 9) of treated animals.

Example 2

Gross and Light Microscopic Appearance of Synovial Grafts in SCID Mice

Figure 1:
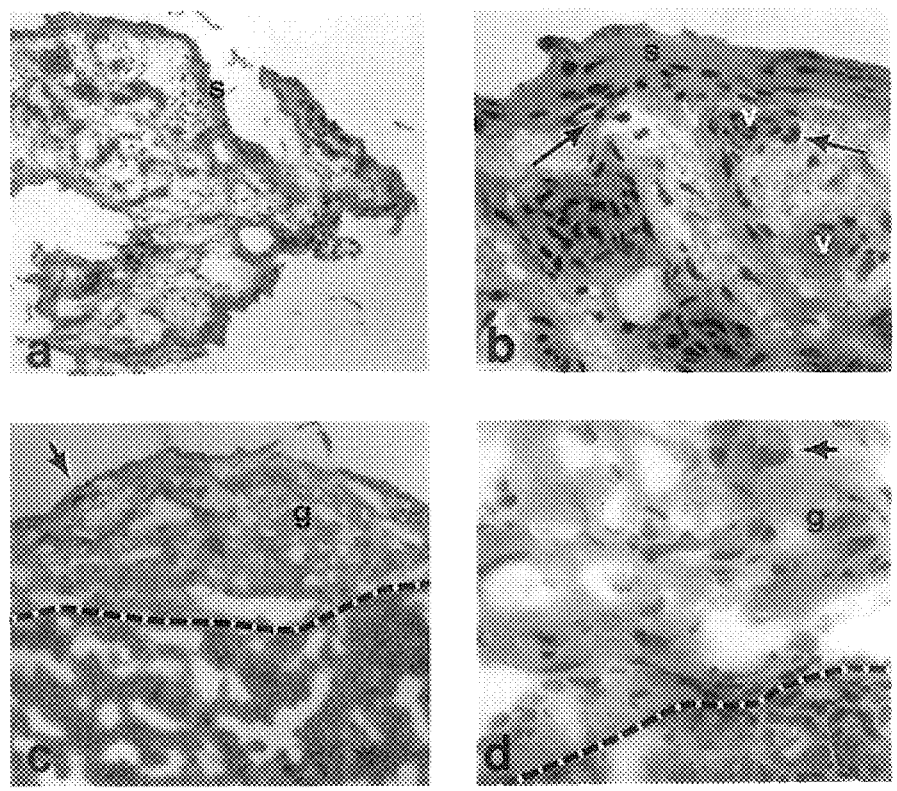
FIGS. 1(A–D): Morphology of Fresh Normal Synovium and Normal Synovial Xenografts in SCID Mice. Panel a shows low power view (×100) and Panel b shows a higher magnification (×400) of a hematoxylin and eosin (H and E) stained tissue section of fresh normal synovium no. 28 prior to engraftment. A thin layer of type A synovial lining cells (S), numerous vessels (V) and scattered mononuclear cells (arrows) are present. Panel c shows lower power (×100) and panel d, a higher power (×400) view of synovial xenograft no. 28–3, 5 weeks following implantation of synovium no. 28 under the renal capsule. Graft 28–3 appears above the renal parenchyma, and the dotted line shows graft-kidney interface. Arrow in panel c shows renal capsule over graft, g indicates graft. Arrow in panel d indicates mononuclear cell within graft.

Engrafted normal synovium increased in size 2 to 3 fold over 6 weeks under the renal capsule. The histologic morphology of engrafted normal synovium (FIGS. 1c and 1d) was similar to that of fresh normal synovium no. 28 prior to engraftment (FIGS. 1a an 1b), and contained predominantly synovial fibroblasts and vessels with only rare mononuclear cells seen.

Figure 2:
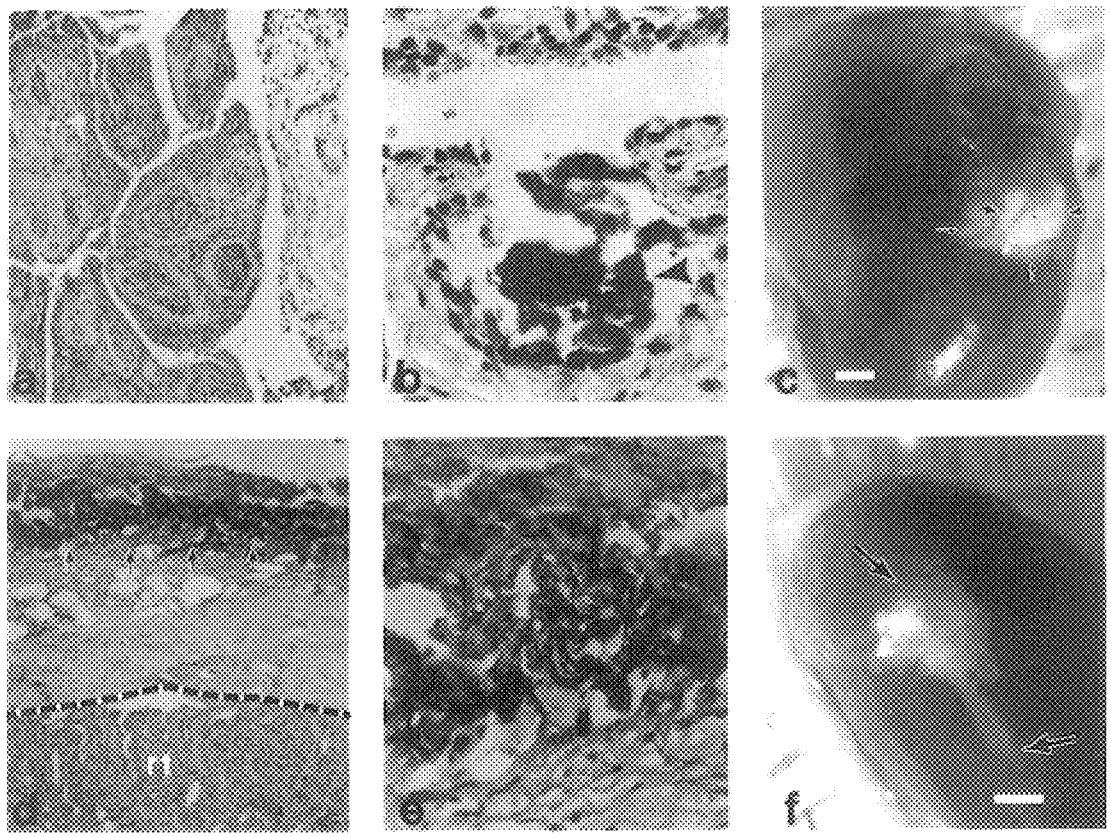
FIGS. 2(A–F): Morphology of Fresh RA Synovial Tissues and RA Synovial Xenografts in SCID mice. Panel a shows a fresh synovium no. 27 stained with H and E, ×100. Panel b shows an H and E of the same specimen at a higher power, ×400, with arrowhead showing an area of calcium deposition. Panel c shows a freshly harvested SCID mouse kidney containing synovial graft 27-6 six weeks after implantation of fresh synovium 27. Arrows indicate the border of the graft; larger arrowheads indicate a large plaque-like calcific deposit within the graft. White bar=1 mm. Panel d shows an H and E stain of the synovium xenograft 27-6, ×100, showing the calcific deposit seen grossly in panel c. Graft appears above the renal parenchyma, and the dotted line indicates graft-kidney interface. Arrows indicate regions of darkly staining extracellular deposits near the surface of the graft; rt indicates renal tubules. Panel e shows a higher power micrograph of an H and E-stained section of the same specimen, ×400, showing more detail of the densely staining deposits seen in panel d. Panel f shows a freshly harvested SCID mouse kidney containing synovial graft 27-7, six weeks after implantation of fresh synovium 293. Top arrow indicates the upper border of the graft; bottom arrow indicates an extension of the graft growing along the original track of placement. White bar=1 mm.
Figure 3:
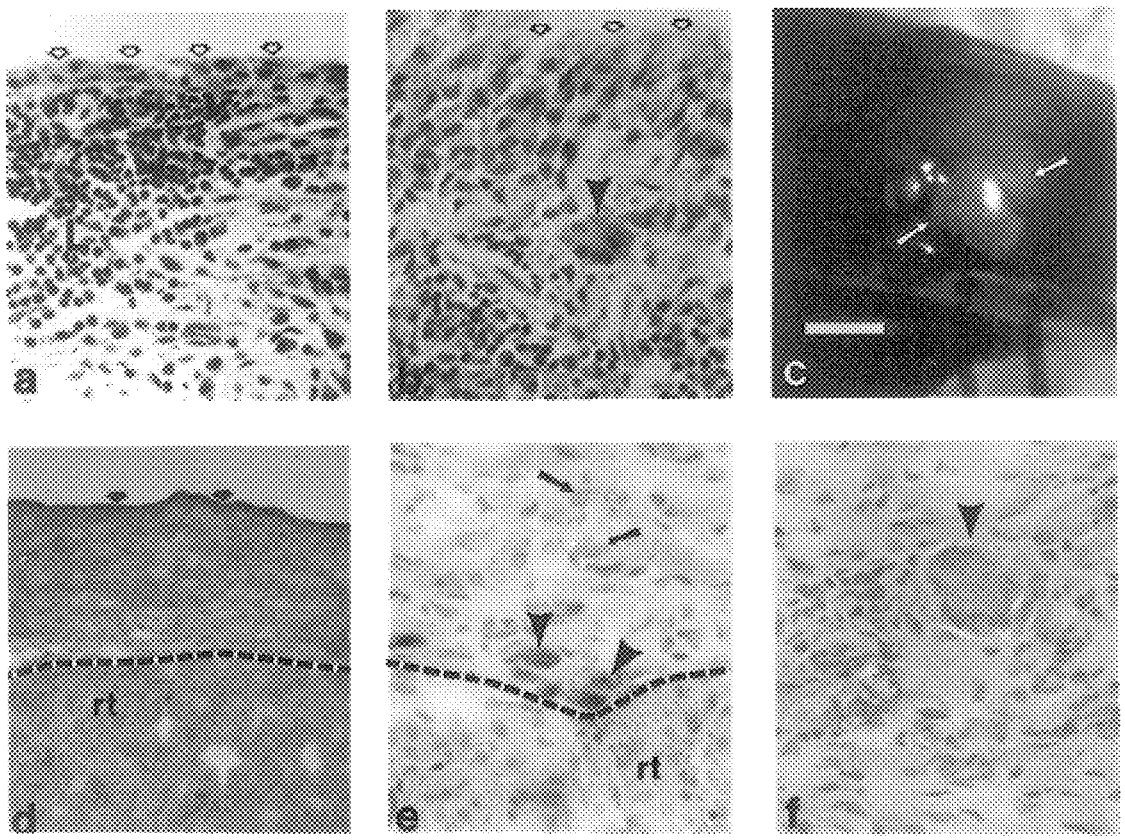
FIGS. 3(A–F): Morphology of fresh JRA Synovial Tissue and JRA Synovial Xenografts in SCID mice. Panel a shows fresh synovium no. 21 stained with H and E, ×400. L indicates infiltration of lymphocytes, arrows indicate type A synovial lining cells on the surface of the specimen. Panel b shows an H and E-stained section of the same specimen (×400).

Similar to normal synovial tissue, synovial tissue from RA and JRA patients often increased in size 2–3 fold over 5–9 weeks under the renal capsule (FIGS. 2 and 3). Human RA synovial grafts were well vascularized, and in some cases extended back along the original tract of graft placement (FIG. 2f). Interestingly, the histologic morphology of RA synovial grafts contained components of fresh RA synovial tissue no. 27 (FIG. 2). Synovial fibroblasts and vessels were present in RA synovial grafts, although mononuclear cells were less prominent in RA synovial grafts than in fresh synovial tissue (FIG. 2 and Table 4). Fresh RA synovium had small focal areas of calcification (FIG. 2b) as did 3 of 7 RA grafts. In one RA graft (no. 27-6) a large (2×3 mm) calcified plaque protruded from the surface of the graft (FIG. 2c).

Similar to RA tissue no. 27, fresh JRA synovium no. 21 had synovial cell proliferation, mononuclear cell aggregates, multinucleated giant cells, and numerous pigmented macrophages preset (FIG. 3). Synovial grafts derived from JRA synovium no. 21 (nos. 21-2 to 21-10) also contained numerous multiculeated giant cells, pigmented macrophages, foci of lymphocytes and diffuse areas of macrophage infiltration (FIG. 2). Grafts derived from HLA-B27− related spondyloarthropathy tissue no. 42 after 6 weeks contained no inflammatory cells.

Example 3

Phenotypic Analysis of Human Synovial Xenografts Derived From Normal Synovium

Fresh normal synovium no. 28 contained fibroblasts, vessels and sporadic macrophages but was devoid was devoid of infiltrating T and B cells (Table 2). Normal synovial grafts nos. 28-2, 28-3, and 28-4 were similar in phenotype to pre-implantation synovium (Table 2). Vessels and fibroblasts were CD44+, CD 29+ and human fibronectin+ both in fresh synovium no. 28 and in normal no. 28 synovial grafts (Table 3). In general, vessels in fresh synovium no. 28 and in normal no. 28 synovial grafts were CD54 (ICAM-1)-(Table 3, FIGS. 3c and 3d). Fibroblasts in fresh normal synovium no. 28 were cD71 (transferrin receptor)−, but were CD71+ in 3 of 3 normal synovial grafts studied (Table 3), suggesting induction of synovial fibroblast proliferation in human synovial grafts.

Example 4

Phenotypic Analysis of Human Synovial Grafts Derived From Inflammatory Arthritis Synovial Tissue Implanted into SCID Mice Both JRA and RA synovial grafts contained large numbers of macrophage (Tables 4 and 5, FIG. 4b). All grafts of JRA synovium contained scattered T cells that were predominantly CD4+ and uniformly TCRβ+. TCRδ+ cells were not seen in grafts nor in fresh JRA synovium no. 21 (Table 4). In contrast, RA and B27+ spondyloarthropathy synovial grafts from mice that did not receive and IP injection of human PBMC contained rare to no lymphocytes, although both CD4+ and CD8+ T cells were present in fresh synovia nos. 27, 29, 30, and 42.

Inflammatory arthritis synovial grafts expressed high levels of human MHC Class I and Class II monomorphic and polymorphic determinants (FIGS. 4e and 4f, Table 5). Using indirect IF analysis with a large panel of anti-human MHC Class I and Class II mAbs that did not react with SCID mouse tissues, synovial grafts expressed the same MHC polymorphic determinants as the fresh synovial tissue from which the grafts were derived.

With regard to the expression of cell adhesion and cell activation markers, inflammatory synovial grafts differed from normal synovial grafts (Tables 3 and 5). Vessels in JRA and RA grafts, in contrast to normal synovial grafts, were generally CD54 (ICAM-1)+ and CD58 (LFA-3)+ (Table 5, FIGS. 3c, 3d, 3e).

Example 5

Analysis of Murine Immune Cells in Human Synovial Grafts and Analysis of Human Immune Cells in SCID Mouse PB Lymphoid Organs All nine JRA grafts were assayed in indirect IF assays for the presence of murine macrophages and murine T cells: 3 grafts contained no murine macrophages while 6 contained scattered (<10 cells/section) murine macrophages. Four of the JRA synovial grafts tested contained murine CD3ε+, TCRβ+ T cells in numbers ranging from 2 to 12 per graft section. In five RA grafts that were also examined for the presence of murine macrophage and murine T cells, no macrophages were found; one RA graft contained rare murine T cells.

To address the possibility of human immune cells leaving the synovial xenograft and migrating to mouse tissues, mouse thymus, spleen, and liver of 4 animals (nos. 21-8, 21-9, 21-10, and 27-2) were tested in indirect immunofluorescence assays for the presence of human cells reactive with mAbs against human CD45, CD3ε; CD4, CD8, and TCRαβ. None of these mice had undergone IP injections of human PBMC. No human cells expressing these markers were found in mouse liver, spleen, or thymus. Similarly, using an anti-human mAb against human CD45 flow cytometric analysis of mouse PB mononuclear cells from engrafted animals (nos. 27-1, 27-2, 27-3, 27-4, 27-6, 27-7, 27-8, 28-2, 28-3, 28-4, and 28-5) detected few circulating human cells in engrafted SCID mice. Whereas, $40.0\pm20.1\times10^3$ cells mm3 were CD45+ in untreated experiment 27 animals, only rare CD45+ cells were detected in the PB of anti-asialo GM-1 treated animals ($10.3\pm8.7\times10^3$ cells/mm$^3$). Similar numbers of CD45± cells were detected in PBL in experiment 28 mice engrafted with normal synovial ($20.0\pm3.7\times10^3$ cells/mm$^3$).

Example 6

Assay for mRNA of Metalloproteases and Tissue Inhibitor of Metalloprotease (TIMP) In Engrafted Human Synovium Using In Situ Hybridization Nine synovial grafts and the three fresh synovial tissues from which the grafts were derived (synovia Nos. 21, 27 and 28) were studied in situ hybridization assays for mRNA for the proinflammatory protease, collagenase, stromelysin and 72 KD– gelatinase and for the anti-inflammatory molecule, tissue inhibitor of metalloprotease (TIMP). It was found that RA and JRA fresh synovium produced collagenase, stromelysin, gelatinase and TIMP mRNA predominantly in peripheral type A synovial lining cells, as previously described for collagenase and stromelysin. (Haynes et al, Hum. Immunol. 4:273 (1982); Oberdan et al, Proc. Natl. Acad. Sci. USA 84:1374 (1987)). In contrast, collagenase and stromelysin mRNA production by cells in synovial grafts in SCID mice was markedly decreased or absent compared to that in fresh synovium (Table 6). However, foci of gelatinase (type IV collagenase) and TIMP mRNA expression could be found in some grafts that were equivalent to areas in fresh synovial tissue (FIG. 6). Neither fresh nor engrafted normal synovium expressed mRNA for TIMP or for proteases (Table 6).

Example 7

In Vivo Treatment of SCID MIce Engrafted with Human Synovium with IP Pulse Corticosteroid Therapy Three animals (27-4, 27-7, 27-8) engrafted with RA synovium were treated with a pulse cortiscosteriod regime of 3 daily IP injections of 10 mg/kg of hydrocortisone sodium succinate. The histologic morphology of grafts 27-4, 27-7, and 27-8 were compared in indirect IF assay using the mAbs described in Tables 4 and 5. The 27 series of grafts did not contain numerous lymphocytes or macrophages (as did the 21 series of grafts) such that the effect of pulse corticosteroid therapy on graft lymphocyte and macrophage populations could not be assessed in this series of experiments. Using mAbs against fibronectin, CD44 and VLβ, no difference was seen in grafts from treated versus untreated animals (FIG. 7). However, a striking decrease in fibroblast transferring receptor expression was seen in all three synovial grafts from animals treated with pulse corticosteroids compared to experiment 27 or 21 grafts from animals not treated with pulse cortisteroids (FIGS. 7c–d)

Example 8

Migration of Autologous and Allogeneic Human PB T cells to Human Synovial Grafts and to SCID Mouse Lymph Nodes One of the characteristics of inflammatory synovial grafts compared to preimplantation synovium was the disappearance of T lymphocytes from the grafts over time. This result was used to study T cells capable of migration to synovium. Experiments were performed in which mice engrafted with human synovium from patients with HLA B27– RA or HLA B27+ spondyloarthropathy received a single IP injection of either normal human HLA B27+ PBMC, or in the case of HLA B27+ spondyloarthropathy tissue no. 42, received autologous B27+ PBMC (Table 7). After 7 days, grafts were harvested and analyzed for the presence of injected allogeneic or autologous B27+ PBMC lymphocytes.

Initially, different numbers of fresh or Con A– activated allogeneic PBMC were used in the injections of mice bearing B27– RA synovial grafts to derive an optimal dose regimen. The optimal regimen was an IP injection of $50\times10^6$ PBMC, with which synovial grafts contained>100 B27+ PBMC cells per graft section (FIG. 5). No differences were seen using fresh versus Con A-activated PBMC. Human PB cells were confined to the graft, and were not found in surrounding renal parenchyma, nor in liver, spleen, thymus, appendix, or peripheral blood of injected animals.

However, murine abdominal lymph nodes were found adjacent to the kidney of one animal (29-4) and the spleen of another (29-11), and both lymph nodes contained B27+ human PB T lymphocytes (FIGS. 6 and 7). Similarly, when $50\times10^6$ fresh autologous PBMC were injected into SCID mice bearing B27+ spondyloarthropathy synovium no. 42, a parasplenic lymph node was found in each of two animals (42-5 and 42-7), and both lymph nodes contained B27+ human T lymphocytes from patient no. 42.

T cells found in SCID mouse lymph nodes were compared with the phenotype of T cells from the synovial graft in the same animal (Table 8). Human T cells in SCID lymph nodes were predominantly CD4+ (87 to 90%), whereas T cells in 2 of 3 grafts either contained (graft no. 29-4) or grew in culture (graft no. 42-5) populations of T cells containing CD8+ cells (Table 8). Only graft and LN no. 29-4 were available for direct comparison of uncultured homed T cells. Whereas 25% of T cells in 29-4 graft were Vβ8, only 2% of LN cells were Vβ 8 (Table 8).

Example 9

In Vitro Growth of Human T cells from Synovial Xenografts in SCID Mice

Table 9 shows the phenotype of normal no. 10 B27+ human PB T cells grown in vitro 14–21 days that migrated to synovial grafts in vivo. Whereas fresh PB T cells from normal donor no. 10 had a normal CD4/CD8 ratio, there was a preponderance of CD4+ cells in T cells grown from grafts 29-9 and 29-11, while T cells grown from graft no. 30-11 had a 2:1 CD4/CD8 ratio. T cells grown from grafts 30-11 and 29-9 had higher Vβ6.7 and Vβ8 representation, respectively, compared with fresh normal no. 10 T cells (Table 9). As a control, normal no. 10 PBMC grown in vitro for 14 days (never having been injected into SCID mice) were 70% CD8+ and 10% CD4+ (Table 9), suggesting the CD4+ predominance of T cells cultured from synovial grafts was not due solely to in vitro culture or PBMC.

Table 10 shows the phenotypic analysis of fresh T cells from normal B27+ donor no. 10 and B27+ spondyloarthropathy patient no. 42 compared with T cells grown from synovial grafts present in the animals that received either normal allogeneic no. 10 PBMC cells (42-2, 42-3, 42-4) or received patient 42 autologous T cells (42-5). To determine that PBMC cells from 42-2, 42-3, and 42-4 grafts were from normal donor no. 10 and not from synovium no. 42 T cells, an HLA panel of mAbs were tested on normal no. 10 fresh PBMC, cell lines 42-2, 42-3, and 42-4 and on fresh synovial tissue no. 42. All T cells grown from grafts 42-2, 42-3, and 42-4 were found to be from normal donor no. 10. Unlike T cells that grew from RA grafts no. 29 and 30, allogeneic normal no. 10 T cells that migrated to synovium no. 42 and grew in vitro were 47–64% CD8+.

Example 10

Southern Blot Analysis of T Cells that Migrated to RA and B27—Related Spondyloarthropathy Synovial Grafts in SCID Mice FIGS. 8A and 8B show Southern blot analysis of DNA extracted from T cells grown from synovial xenografts, digested with either EcoRI, Hind III, or Bam HI restriction enzymes and probed with a constant region cDNA of TCRβ (Cβ). Whereas fresh normal no. 10 (FIG. 8A) and patient no. 42 PBMC DNA (FIG. 8D) showed no discrete arranged TCRβ gene bands, DNA from 29-11, 30-11, and 29-9 (FIG. 8A) and from 42-2, 42-3, 42-4, and 42-5 (FIG. 8B) all showed multiple TCR rearrangement bands with each restriction enzyme, indicting the oligoclonal nature of human T cells grown from synovial grafts. Importantly, PB T cell DNA from normal donor no. 10 and from patient no. 42 grown in culture for 14 days, having never been injected into SCID mice, also showed oligoclonal bands on Southern blot analysis (FIGS. 8C and 8D). These data indicated that the TCRβ bands seen in oligoclonal DNA from T cells grown from synovial grafts could not solely be attributed to the restricted nature of T cell migration, but could also be due to selection of restricted numbers of T cell clones by in vitro culture. However, rearranged TCRβ band in 6 of 7 of no. 10 and all 4 of no. 42 T cell suspensions grown from migrated T cells were different from those seen in control cultured PBMC. Taken together with the phenotypic differences in control T cells cultured in vitro and T cells cultured from grafts, these data suggest that different populations of T cells migrated to synovial grafts compared to T cells that grew from control no. 10 or patient no. 42 PBMC in vitro (Tables 9 and 10 and FIG. 8).

Example 11

Analysis of TCR Vβ mRNA Expression of T Cells Grown from Synovial Xenografts

To study the TCR Vβ usage of human T cells grown from synovial grafts, mRNA was extracted from T cells grown from graft nos. 29-9, 29-11, 30-11, 42-2, 42-3, 42-4, and 42-5, and analyzed in reverse PCR using oligonucleotide primers specific for TCR Vβ subfamilies (Wucherpfennig et al, *Science* 248:1016 (1990); Choi et al, *Proc. Natl. Acad. Sci. USA* 86:8941 (1989); Hall et al, *Biotechniques*. In press). Whereas normal no. 10 T cells were limited in TCR Vβ expression (4 to 8 Vβ types detected) when grown from RA graft nos. 29-9, 29-11, and 30-11, when no. 10 T cells were grown from graft nos. 42-2, 42-3, or 42-4 they were less restricted in TCR Vβ expression (16-22 Vβ types detected) (FIG. 9C). Patient 42 T cells grown from an autologous synovial graft 42-5, however, were markedly restricted with only 4 TCR Vβ represented, Vβ1, Vβ11, Vβ13.2 and Vβ20 (FIGS. 9B and 9C).

TCR Vβ analysis of control (not injected in mice) normal no. 10 PB T cells and control no. 42 PB T cells grown in vitro for 14 days showed all TCR Vβ types present (FIG. 9C).

Comparison of the results of Vβ typing by FACS analysis and by PCR analysis of the cultured T cells revealed concordant data, with only three exceptions (Tables 9, 10, and FIG. 9B). Two percent of T cells grown from graft 30-11 were 42 1C1 (Vβ5)+, through PCR analysis of mRNA from these T cells did not detect this Vβ type. Conversely, Vβ+ T cells were detected by PCR in 30-11 T cells but not by FACS analysis. Also, 1% of T cells grown from graft 29-9 were 42-1C1 (Vβ5)+, with negative results for detection of they Vβ type on PCR analysis of mRNA from these cells.

The entire contents of all documents cited hereinabove are hereby incorporated by reference.

One skilled in the art will appreciate that although the Examples set forth above involve forms of RA synovium tissue, synovial tissue and other inflammation tissue types from other clinical forms of inflammatory synovitis (such as systemic lupus erythromatosis and Reiter's syndrome and psoriasis) can also be used. Further, one skilled in the art will appreciate that tissue from other organs involved in the inflammatory process, such as cornea and sclera tissue, that become inflamed during the course of autoimmune disease (e.g. RA and systemic lupus erythromatosis), can be used.

TABLE 1

Engraftment of Human Synovial Tissue in SCID Mice

| Immunosuppressive Treatment of SCID Mice | Exp. 21, JRA Synovium (n = 10) | Exp. 27, RA Synovium (n = 7) | Exp. 28, Normal Synovium (n = 4) | Total | |
|---|---|---|---|---|---|
| | (no. of mice engrafted/no. of mice operated) | | | | |
| Anti-asialo GM-1 | 4/5 | 4/4 | ND | 8/9 | (89%) |
| No treatment | 5/5 | 3/3 | 4/4 | 12/12 | (100%) |

*Experiment 21 mice were engrafted with JRA synovium no. 21. Experiment 27 mice were engrafted with RA synovium no. 27. Experiment 28 mice were engrafted with normal synovium taken at the time of hallux valgus surgery from patient no. 28.

TABLE 2

Phenotypic Analysis of Human Normal Synovium Xenografts In SCID Mice

| Tissue | Macrophages | T cells | | | | | | B cells | | Fibroblasts | Vessels |
|---|---|---|---|---|---|---|---|---|---|---|---|
| | CD11b | CD7 | CD3 | CD4 | CD6 | TCRδ | TCRβ | B1 | B2 | TE7 | V2 |
| Fresh Synovium no. 28 | + | − | − | − | − | − | − | − | − | + | + |
| Graft no. 28-2 | − | − | − | − | − | − | − | ND | − | + | − |
| Graft no. 28-3 | + | − | − | − | − | − | − | − | − | + | + |
| Graft no. 28-4 | ± | − | − | − | − | − | ND | − | + | − | + |

+ = greater than 10 cells/HPF reactive with mab in IF assay; ± = 1 to 10 cells/HPF reactive with mAb in IF assay; − = no reactivity with mAb in entire graft. CD11b = Mo-1; CD7 = 3ALe; CD3ε = Leu4; TCRβ = βF1; TCRδ = TCRδ1. Grafts 28-2, 28-3 and 28-4 were made using fresh synovium no. 28.

TABLE 3

Expression of Cell Adhesion and Activation Molecules By Normal Synovial Xenografts in SCID Mice

| Tissue | Molecule Assayed | | | | | | | | | |
|---|---|---|---|---|---|---|---|---|---|---|
| | CD44 | CD2 | CD58 | CD54 | CD11a | CD29 | FN | CD71 | CD25 | HLADR |
| Fresh Synovium no. 28 | + | − | − | − | − | + | + | − | − | + |
| Graft no. 28-2 | + | − | − | − | − | + | + | − | − | − |
| Graft no. 28-3 | + | − | − | ± | − | + | + | + | − | + |
| Graft no. 28-4 | + | − | − | − | − | + | + | ± | − | + |

+ = greater than 10 cells/HPF reactive with mAb in IF assay; ± = 1 to 10 cells/HPF reactive with mAb in IF assay; − = no reactivity with mAb in entire graft. CD58 = LFA-3; CD54 = ICAM-1; CD11a = LFA-1; CD29 = VLAβ1, FN = fibronectin mAb FN15; CD25 = TAC (IL2Rα); HLA DR = L243; CD71 = transferrin receptor mAb, 5E9; CD2 = E rosette receptor mAb 9-1. Graft nos. 28-2, 28-3 and 28-4 were using synovium no. 28.

TABLE 4

Phenotypic Analysis of Human JRA and RA Synovium Xenografts In SCID Mice

| Tissue | Macrophages | T cells | | | | | | B cells | | Fibroblasts | Vessels |
|---|---|---|---|---|---|---|---|---|---|---|---|
| | CD14 | CD7 | CD3ε | CD4 | CD8 | TCRδ | TCRβ | B1 | B2 | TE7 | V2 |
| Fresh Synovium no. 21 (JRA) | + | + | + | + | ± | − | + | + | − | + | + |
| Graft no. 21-2 | + | + | + | + | + | − | + | − | − | + | + |
| Graft no. 21-6 | + | + | + | + | − | − | + | − | − | + | + |
| Graft no. 21-8 | + | + | + | + | ± | − | + | + | + | + | + |
| Fresh Synovium no. 27 (RA) | + | + | + | + | + | ± | + | − | − | + | + |
| Graft no. 27-2 | ± | − | − | ± | − | − | − | − | − | + | + |
| Graft no. 27-3 | − | − | − | − | − | − | − | . | − | + | + |

+ = greater than 10 cells/HPF reactive with mAb in IF assay; ± = 1 to 10 cells/HPF reactive with mAb in IF assay; − = no reactivity with mAb in entire graft. CD14 = LeuM3; CD7 = 3Ale; CD3ε = Leu4; TCRβ = βF1; TCRδ = TCRδ1. Grafts 21-2, 21-6 and 21-8 were made using JRA synovium no. 21, graft nos. 27-2 and 27-3 were made using RA synovium no. 27. RA = rheumatoid arthritis; JRA = juvenile rheumatoid arthritis.

TABLE 5

Expression of Cell Adhesion and Activation Molecules by JRA and RA Synovial Xenografts in SCID Mice

| Tissue | Molecule Assayed | | | | | | | | | |
|---|---|---|---|---|---|---|---|---|---|---|
| | CD44 | CD2 | CD58 | CD54 | CD11a | CD29 | FN | CD71 | CD25 | HLADR |
| Fresh Synovium no. 21 (JRA) | + | + | + | + | + | + | + | + | ± | + |
| Graft no. 21-2 | + | + | + | + | + | + | t | + | + | + |
| Graft no. 21-6 | + | + | + | + | + | + | + | + | + | + |
| Graft no. 21-8 | + | + | + | + | + | + | + | + | . + | |
| Fresh Synovium no. 27 (RA) | + | + | + | + | + | + | + | + | ± | + |
| Graft no. 27-2 | + | ± | + | + | ± | + | + | + | ± | ± |
| Graft no. 27-3 | + | – | – | – | + | + | + | + | – | – |

+ = greater than 10 cells/HPF reactive with mAb in IF assay; ± = 1 to 10 cells/HPF reactive with mAb in IF assay; – = no reactivity with mAb in entire graft. CD 58 = LFA-3; CD54 = ICAM-1; CD11a = LFA-1; CD29 = VLAβ; FN = fibronectin mAb FN15; CD25 = TAC, (IL2Rα); HLADR = L243; CD71 = transferrin receptor antibody 5E9; CD2 = E-rosette receptor mAb 9-1. Graft nos. 21-2, 21-6 and 21-8 were made using synovium no. 21, graft nos. 27-2 and 27-3 were made using synovium no. 27.

TABLE 6

Detection of Protease and TIMP mRNA in Fresh Human Synovial Tissue and in Human Synovial Grafts in SCID Mice

| Tissue (Diagnosis) | mRNA Species Identified Using In Situ Hybridization | | | |
|---|---|---|---|---|
| | Collagenase | Stromelysin | Gelatinase | TIMP |
| Fresh Synovium no. 21 (JRA) | + | + | + | + |
| Graft no. 21-6 | – | – | + | + |
| Fresh Synovium no. 27 (RA) | + | + | + | + |
| Graft no. 27-1 | – | – | + | + |
| Graft no. 27-2 | – | – | + | + |
| Graft no. 27-3 | – | – | + | + |
| Graft no. 27-7 | – | – | + | + |
| Graft no. 21-8 | – | – | + | + |

TIMP - Tissue Inhibitor of Metalloproteases.
+ = Silver grains present > background silver grains using antisense probes.
– = Silver grains present E background silver grains using antisense probes.
21 series of grafts from synovium no. 21; 27 series grafts from synovium no. 27.

TABLE 7

Experiments Involving Injection of Normal Allogeneic or Spondyloarthropathy Autologous HLA B27+ PBMC Into SCID Mice Bearing Synovial Grafts

| Synovial Graft Source | PBMC Source | Number Injected | Number of Grafts Placed in Culture | Animals From whom T Cells Grew |
|---|---|---|---|---|
| RA no. 29 (B27–) | Normal no. 10 (B27+) | 7 | 3 | 29-9, 29-11 |
| RA no. 30 (B27–) | Normal no. 10 (B27+) | 8 | 3 | 30-11 |
| B27-related spondyloarthropathy no. 42 | Normal no. 10 (B27+) | 3 | 3 | 42-2, 42-3, 42-4 |
| B27-related spondyloarthropathy no. 42 | B27-related spondyloarthropathy no. 42 | 3 | 3 | 42-5 |

TABLE 8

Comparison of Human T Cells Found in SCID Lymph Nodes and Human Synovial Grafts 29-4, 29-11, 42-5, and 42-7

| | % of Cells Positive for Marker | | | | | | | |
|---|---|---|---|---|---|---|---|---|
| | 29-4 | | 29-11* | | 42-5* | | 42-7* | |
| Marker (mAb) | Graft | LN | Graft | LN | Graft | LN | Graft | LN |
| Vβ5 (142-1C1) | 0 | 1 | 0 | 1 | 2 | 1 | NA | 1 |
| Vβ6.7 (OT145) | 2 | 2 | 9 | 8 | 0 | 1 | NA | 0 |
| Vβ8 (MX11 or MX9) | 25 | 2 | 7 | 10 | 1 | 1 | NA | 0 |
| CD4 (Leu2a) | 40 | 90 | 89 | 87 | 57 | 89 | NA | 89 |
| CD8 (Leu3a) | 60 | 5 | 6 | 13 | 37 | 11 | NA | 11 |

SCID mice 29-4 and 29-11 were implanted with RA synovium no. 29; four to five weeks after surgery and one week before harvest, mouse 29-4 received an IP injection of $10 \times 10^6$ Con A stimulated normal human HLA B27+ allogeneic PBMC, and mouse 29-11 received an IP injection of $35 \times 10^6$ Con A stimulated allogeneic HLA B27+ PBMC. SCID mice 42-5 and 42-7 were implanted with HLA-B27+ spondylarthropathy synovium no. 42; seven weeks after surgery and one week before harvest, each mouse received an IP injection of $50 \times 10^6$ human autologous PBMC.

*Tissue was cultured as tissue retained for histologic analysis did not contain sufficient graft for analysis. Data for 29-11 and 42-5 are from cultured T cells from graft. Data from graft no. 42-7 not available (NA).

TABLE 9

Phenotype of oligoclonal Suspensions of Allogeneic Normal Human HLA B27+ T Cells Grown From Human RA HLA B27− Synovial Grafts 29-9, 29-11, and 30-11

| | Allogeneic Cell Injection of Normal No. 10 PBMC | | | | |
|---|---|---|---|---|---|
| Marker (mAb) | 29-9 | 29-11 | 30-11 | *Fresh Normal no. 10 T Cells | Normal no. 10 PBMC Cells in Culture in vitro 14 days |
| HLA B27 (145.2) | 100 | 100 | 100 | 100 | 100 |
| CD3 (Leu4) | 96 | 93 | 95 | 100 | 98 |
| CD4 (Leu3a) | 96 | 89 | 45 | 63 | 10 |
| CD8 (Leu2a) | 2 | 6 | 27 | 34 | 70 |
| Vβ5 (42-1C1) | 1 | 0 | 2 | 4 | 6 |
| Vβ6.7 (OT145) | 8 | 9 | 14 | 6 | 9 |
| Vβ8 (MX9) | 17 | 7 | 0 | 7 | 9 |

Synovial tissue used for grafts 29-9 and 29-11 was from RA patient no. 29. Tissue used for graft 30-11 was from RA patient no. 30.

*Fresh uncultured PBMC from normal no. 10.

TABLE 10

Phenotype of Oligoclonal Suspensions of Allogeneic and Autologous Human HLA B27+ T Cells Grown From Human HLA B27+ Spondyloarthropathy Synovial Grafts 42-2, 42-3, 42-4, and 42-5

| | Allogenic Cell Injection of Normal No. 10 PBMC | | | | | Autologous Cell Injection of No. 42 PBMC | | |
|---|---|---|---|---|---|---|---|---|
| Marker (mAb) | 42-2 | 42-3 | 42-4 | Fresh no. 10 T cells* | Normal no. 10 PBMC Cells in Culture in vitro 14 days‡ | 42-5 | Fresh no. 42 PB T cells | Patient no. 42 PBMC Cells in Culture in vitro 14 days‡ |
| HLA B27 (145.2) | 100 | 100 | 100 | 100 | 100 | 100 | 100 | 100 |
| CD3 (Leu4) | 91 | 98 | 100 | 100 | 98 | 94 | 100 | 89 |
| CD4 (Leu3a) | 47 | 41 | 33 | 63 | 10 | 57 | 34 | 10 |
| CD8 (Leu2a) | 47 | 48 | 64 | 34 | 70 | 37 | 60 | 79 |
| Vβ5 (42-1C1) | 2 | 2 | 2 | 4 | 6 | 2 | 10 | 2 |
| Vβ6.7 (OT145) | 1 | 5 | 9 | 6 | 9 | 0 | 2 | 2 |
| Vβ8 (MX9) | 4 | 21 | 3 | 7 | 9 | 1 | 2 | 1 |
| Vβ12 (S511) | 1 | 0 | 5 | ND | 3 | 0 | 2 | 2 |
| TCRδ1 | 1 | 1 | 0 | 1 | 11 | 1 | 11 | 1 |
| WT31 | 100 | 99 | 100 | 100 | 84 | 100 | 88 | 100 |

‡These control cells were cultured in vitro directly, without ever having been in SCID mice.
ND = Not done.

What is claimed:

1. A severe combined immunodeficiency disease (SCID) mouse comprising human synovium tissue engrafted under its renal capsule, wherein said engrafted synovium tissue is viable.

2. The mouse according to claim 1, wherein said synovial tissue is inflamed.

3. A method of determining the anti-inflammatory potential of an agent comprising administering said agent to said mouse according to claim 2 and assaying for any change in the inflammatory state of said tissue.

4. A method of assaying the homing or migration of human T lymphocytes comprising:

administering said human T lymphocytes to a SCID mouse comprising human synovium tissue engrafted under its renal capsule, wherein said engrafted synovium tissue is viable; and determining the presence or absence of said T lymphocytes in said tissue.

* * * * *

SEQUENCE LISTING (1) GENERAL INFORMATION:

(iii) NUMBER OF SEQUENCES: 3

```
(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

ACAACCTGAC TATCACCATG                                               20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CGAGCATCTG TGCCATCCTT                                               20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TGTTCCCACC CGAGGTCGCT                                               20
```